(12) United States Patent
Srivastava et al.

(10) Patent No.: US 11,492,414 B2
(45) Date of Patent: Nov. 8, 2022

(54) ERG MONOCLONAL ANTIBODIES

(71) Applicant: The Henry M. Jackson Foundation for the Advancement of Military Medicine, Inc., Bethesda, MD (US)

(72) Inventors: Shiv Srivastava, Potomac, MD (US); Shyh-Han Tan, Kensington, MD (US); Albert Dobi, Rockville, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 699 days.

(21) Appl. No.: 16/277,687

(22) Filed: Feb. 15, 2019

(65) Prior Publication Data

US 2019/0185576 A1 Jun. 20, 2019

Related U.S. Application Data

(60) Division of application No. 14/287,599, filed on May 27, 2014, now abandoned, which is a continuation of application No. 13/266,908, filed as application No. PCT/US2010/032714 on Apr. 28, 2010, now Pat. No. 8,765,916.

(60) Provisional application No. 61/173,834, filed on Apr. 29, 2009.

(51) Int. Cl.
*C07K 16/32* (2006.01)
*G01N 33/574* (2006.01)

(52) U.S. Cl.
CPC ......... *C07K 16/32* (2013.01); *G01N 33/5748* (2013.01); *C07K 2317/56* (2013.01)

(58) Field of Classification Search
None
See application file for complete search history.

(56) References Cited

U.S. PATENT DOCUMENTS

2007/0212702 A1* 9/2007 Tomlins ............... C12N 9/6445
                                                        435/6.16
2009/0010924 A1    1/2009 Wu et al.

FOREIGN PATENT DOCUMENTS

| WO | 2006028655 | 3/2006 |
|---|---|---|
| WO | 2007033187 | 3/2007 |
| WO | 2008094942 | 8/2008 |

OTHER PUBLICATIONS

Burns et al. (Methods in Molecular Biology, vol. 295, 3rd edition, 2005). (Year: 2005).*

Klezovitch, Olga et al., "A casual role for ERG in neoplastic transformation of prostate epithelium", PNAS, Feb. 12, 2008, vol. 105. No. 6, pp. 2105-2110.

Sun, C. et al., "TMPRSS2-ERG fusion, a common genomic alteration in prostate cancer activates C-MYC and abrogates prostate epithelial differentiation", Oncogene, 2008, 27, pp. 5348-5353.

Tanaka, Takeo et al. Efficient generation of antibodies to oncoproteins by using synthetic peptide antigens. Proc. Natl. Acad. Sci. USA, May 1985, vol. 82, pp. 3400-304.

Notice of Reasons for Rejection dated May 14, 2013 from Japanese Application No. 2012-508630, pp. 1-3 (English Translation).

Owczarek, C. M. et al. Detailed mapping of the ERG-ETS2 interval of human chromosome 21 and comparison with the region of conserved synteny on mouse chromosome 16. Gene, 2004, 324: 65-77.

Furusato, B. et al. ERG oncoprotein expression in prostate cancer: clonal progression of ERG-positive tumor cells and potential for ERG-based stratification. Prostate Cancer and Prostatic Diseases, 2010, 13:228-237.

Mohamed, Ahmed A. et al. Ets Family Protein, Erg Expression in Developing and Adult Mouse Tissues by a Highly Specific Monoclonal Antibody. Journal of Cancer, 2010, I:197-208.

Park, Kyung et al. Antibody-Based Detection of ERG Rearrangement— Positive Prostate Cancer. Neoplasia, Jul. 2010, vol. 12, No. 7, pp. 590-598.

Communication from the European Patent Office issued in European Patent Application No. 10770245.8 dated Feb. 1, 2013, 5 Pages.

Hu, Ying et al. Delineation of TMPRSS2-ERG Splice Variants in Prostate Cancer. Clinical Cancer Research, vol. 14, No. 15, Aug. 1, 2008, pp. 4719-4725. XP055036954.

(Continued)

*Primary Examiner* — Meera Natarajan
(74) *Attorney, Agent, or Firm* — MH2 Technology Law Group, LLP

(57) ABSTRACT

Monoclonal antibodies, or antigen-binding fragments thereof, that bind to ERG, and more specifically, to an epitope formed by amino acids 42-66 of ERG3 are disclosed. The monoclonal antibodies can be non-human antibodies (e.g., rabbit or mouse) or humanized monoclonal antibodies having the CDR regions derived from those non-human antibodies. In other embodiments, the monoclonal antibodies are chimeric, having the light and heavy chain variable regions of a non-human ERG antibody. Methods of using the antibodies to detect ERG, or fusion proteins comprising all or part of an ERG polypeptide, such as an ERG polypeptide encoded by a TMPRSS2/ERG, SLC45A3/ ERG, or NDRG1/ERG fusion transcript, are also provided, including methods of detecting ERG or ERG fusion events in a clinical setting. The antibodies can also be used to inhibit the activity of ERG or fusion proteins comprising all or part of an ERG polypeptide, such as an ERG polypeptide encoded by a TMPRSS2/ERG, SLC45A3/ERG, or NDRG1/ ERG fusion transcript and to treat malignancies associated with overexpression of ERG or an ERG fusion event, such as prostate cancer, Ewing's sarcoma, acute myeloid leukemia, acute T-lymphoblastic leukemia, endothelial cancer, and colon cancer.

12 Claims, 19 Drawing Sheets

Specification includes a Sequence Listing.

(56) References Cited

OTHER PUBLICATIONS

Furusato, B. et al. ERG oncoprotein expression in prostate cancer: clonal progression of ERG-positive tumor cells and potential for ERG-based stratification. Prostate Cancer and Prostatic Diseases, vol. 13, No. 29, Jun. 2010, pp. 228-237. XP055050764.

Furusato, Bungo et al. Mapping of TMPRSS2-ERG fusions in the context of multi-focal prostate cancer. Modern Pathology, vol. 21, No. 2, Feb. 1, 2008, pp. 67-75. XP055050765.

Laxman, Bharathi et al. Noninvasive Detection of TMPRSS2:ERG Fusion Transcripts in the Urine of Men with Prostate Cacner. Neoplasia, vol. 8, No. 10, Oct. 1, 2006, pp. 885-888. XP007906803.

Oksana, Yaskiv et al. ERG Protein Expression in Human Tumors Detected With a Rabbit Monoclonal Antibody. Anatomic Pathology, vol. 138, No. 6, Dec. 6, 2012, pp. 803-810. XP009166479.

Murakami, Koko et al. Human ERG-2 protein is phosphorylated DNA-binding protein—a distinct member of the ets family. Oncogene, vol. 8, No. 6, Jun. 1993, pp. 1559-1566. XP009166485.

Fitzgerald, Liesel M. et al. Association of TMPRSS2-ERG gene fusion with clinical characteristics and outcomes results from a population-based study of prostate cancer. BMC Cancer, vol. 8, No. 1, Aug. 11, 2008, pp. 1-10. XP021042869.

Sun, C. et al. TMPRSS2-ERG fusion, a common genomic alteration in prostate cancer activates C-MYC and abrogates prostate epithelial differentiation. Oncogene, vol. 27, No. 40, Sep. 11, 2008, pp. 5348-5353. XP055036926.

Park, Kyung et al. Antibody-Based Detection of ERG Rearrangement—Positive Prostate Cancer. Neoplasia, vol. 12, No. 7, Jul. 2010, pp. 590-598. XP055050757.

Supplementary Search Report from European Patent Application No. 10 77 0245.8 dated Jan. 24, 2013, 4 Pages.

\* cited by examiner

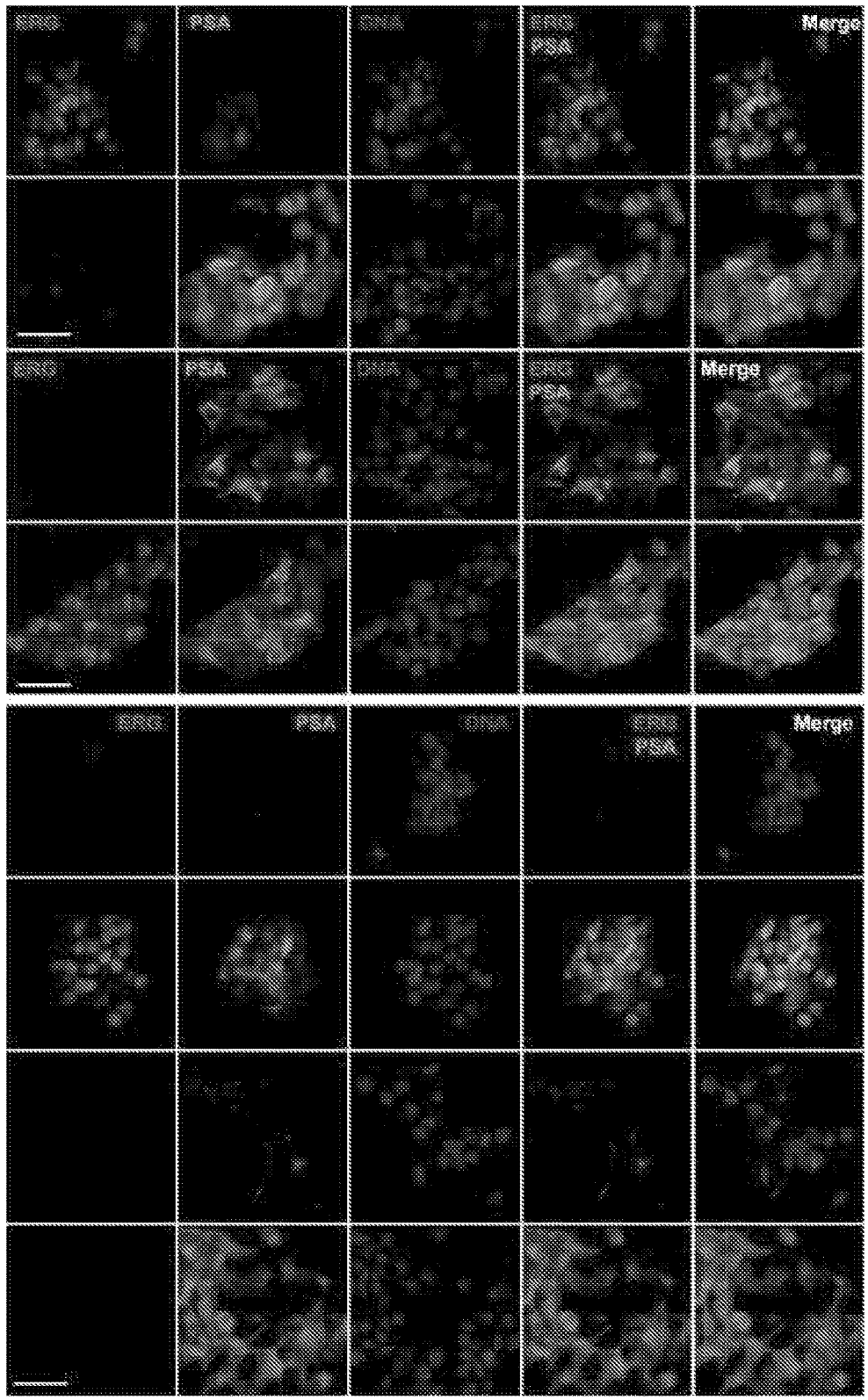

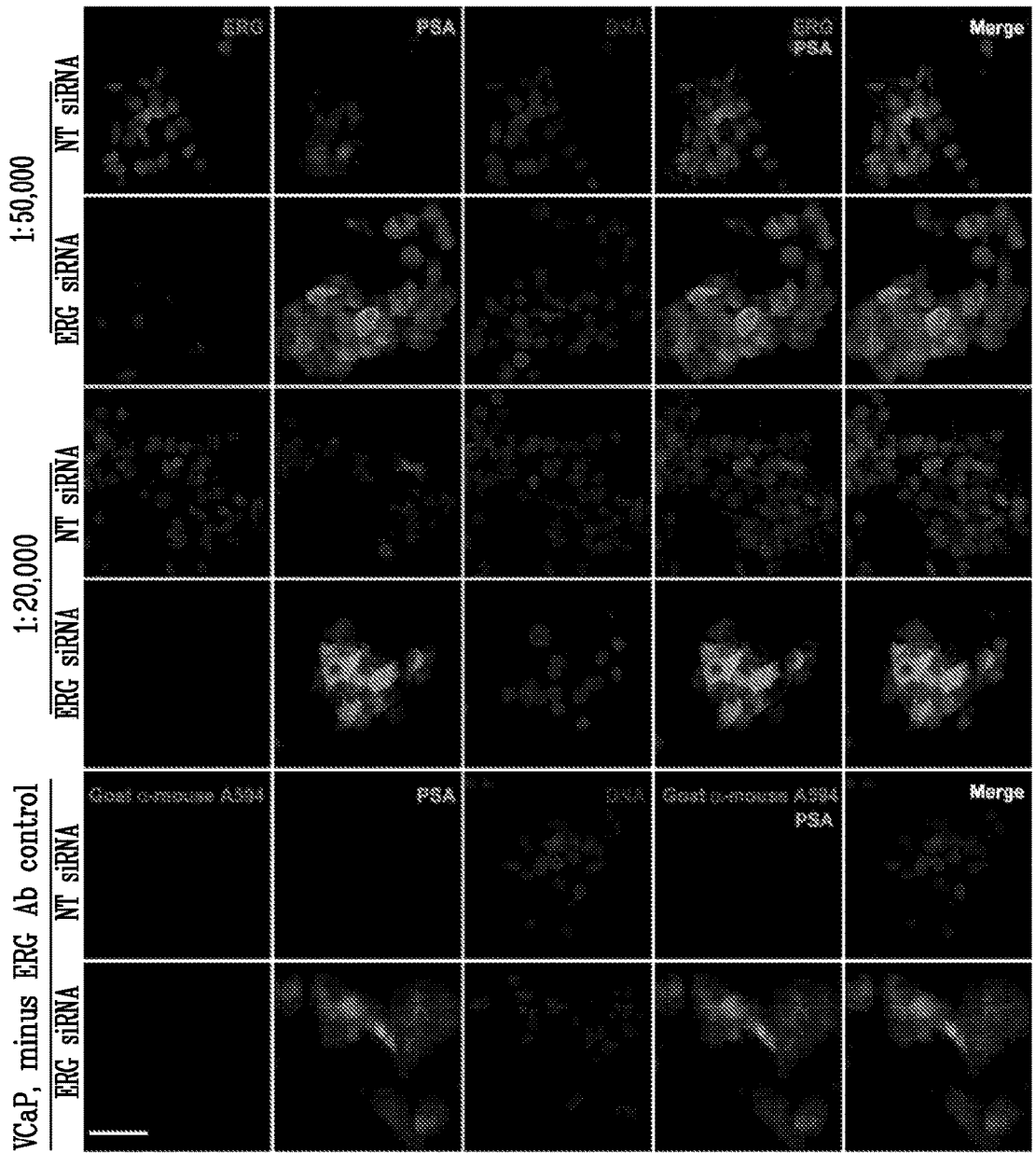

ERG MONOCLONAL ANTIBODIES

CROSS REFERENCE TO RELATED APPLICATIONS

This application is a divisional of U.S. patent application Ser. No. 14/287,599 filed 27 May 2014, which is a continuation of U.S. patent application Ser. No. 13/266,908 filed 28 Oct. 2011 (now U.S. Pat. No. 8,765,916), which is the U.S. National Phase application of International Application PCT/US2010/032714, filed 28 Apr. 2010, which claims the benefit of, and relies on the filing date of, U.S. provisional patent application No. 61/173,834, filed 29 Apr. 2009, the entire disclosure of which is incorporated herein by reference.

STATEMENT OF GOVERNMENT INTEREST

This invention was made with government support under contract number MDA905-04-R-0002 awarded by the Uniformed Services University and grant number CA162383 awarded by the National Institutes of Health and grant number W81XWH-08-1-0532 awarded by the U.S. Army Medical Research and Material Command. The government has certain rights in the invention.

SEQUENCE LISTING

The instant application contains a Sequence Listing which has been submitted electronically in ASCII format and is hereby incorporated by reference in its entirety. Said ASCII copy, created on 2 Feb. 2019, is named HMJ-109-US-02_Sequence_Listing.txt and is 8 Kilobytes in size.

BACKGROUND

The ETS-related gene (ERG) proto-oncogene is overexpressed in 60-70% of prostate tumors as a result of recurring gene fusions involving TMPRSS2 and the ETS family of genes (Petrovics et al., 2005; Tomlins et al., 2005; reviewed in Kumar-Sinha et al., 2008). Emerging studies on human prostate cancer specimens and various experimental models underscore the causative oncogenic function of ERG in prostate cancer (Klezovitch et al., 2008; Tomlins et al., 2008; Sun et al., 2008; Wang et al., 2008). Numerous reports highlighted both diagnostic and prognostic features of the genomic activation of ERG revealing that about half the prostate tumors harbor the most common gene fusion that takes place between the androgen receptor-regulated TMPRSS2 gene promoter and ERG protein coding sequence (reviewed in Kumar-Sinha et al., 2008). Fusion between the TMPRSS2 gene promoter and ERG results in the overexpression of N-terminally truncated or full-length forms of ERG (Klezovitch et al., 2008; Sun et al., 2008). Fusion events between erg and other androgen inducible promoter sequences, such as SLC45A3 (Han et al., 2008) and NDRG1 (Pflueger et al., 2009), have also been identified in prostate cancer.

Poor disease outcome for patients with tumors harboring duplications of TMPRSS2/ERG fusions or chromosomal losses (Edel) associated with the fusion event has been highlighted (Attard et al., 2008; FitzGerald et al., 2008; Mehra et al., 2008) Current diagnosis of prostate cancer is based on a variety of histological features, including architectural growth pattern, loss of basal cells, nuclear atypia, amphophilic cytoplasm, intraluminal blue mucin, pink amorphous secretion, and mitotic figures (Egevad, 2008). If some of these features are not apparent, it can be difficult for pathologists to diagnose prostate cancer, especially in the case of prostate needle biopsies with very limited tumor content (Mostofi et al., 1992; Mostofi et al., 1993). Molecular markers are now being used to aid diagnosis. For example, prostate cancer diagnosis can include basal cell staining of benign glands for specific cytokeratin or p63 (CK903, p63) and tumor cell associated alpha-methyl acyl-CoA-Racemase (AMACR or P504S) (Luo et al., 2002; Rubin et al., 2002). However, these molecular markers have marked limitations in routine diagnosis. Expression of AMACR is found in a variety of other non-malignant lesions, including up to 21% of benign prostatic glands, 58% of nephrogenic adenomas and approximately 18% of cases of atypical adenomatous hyperplasia (Beach et al., 2002; Gupta et al., 2004; Jiang et al., 2001; Yang et al., 2002) New data evaluating ERG over expression and TMPRSS2/ERG genomic rearrangement are providing highly promising new strategies in prostate cancer diagnosis and prognosis (Furusato et al., 2008; Saramaki et al., 2008).

EWS-ERG fusions have been described in a small subset of Ewing's sarcoma, whereas ERG overexpression without fusion was highlighted in acute myeloid leukemia and acute T-lymphoblastic leukemia (Marcucci et al., 2005; Baldus et al., 2006). ERG overexpression has also been linked to megakaryoblastic leukemia (Rainis et el. 2005). Other studies suggest that increased ERG expression plays a role in Alzheimer's Disease (AD) and AD-like neuropathy in Down Syndrome (Shim et al., 2003; Ng et al. 2010).

The structure of the human ERG gene includes at least 17 exons spanning approximately 300 kilobases of genomic sequence and generating at least nine separate transcripts. (Owczarek et al., 2004). The ERGJ-ERG5 isoforms encode five separate polypeptides that can bind the ETS site and act as transcriptional activators. (Owczarek et al., 2004). Of these five isoforms, ERG3 is the longest, encoding a 479 amino acid polypeptide (SEQ ID NO: 1; Accession No. NP_891548.1). The ERG6-ERG9 isoforms represent alternative splice forms with a different 5' exon from other ERG isoforms. While ERG7 and ERG8 have open reading frames, ERG6 encodes multiple stop codons, suggesting that this ERG transcript does not code for a functional protein. (Owczarek et al., 2004). The ERG9 transcript does not contain a putative start codon or a consensus polyadenylation signal suggesting that it might also be a non-coding transcript. (Owczarek et al., 2004).

Although, the ERG proto-oncogene was initially characterized more than twenty years ago (Rao et al., 1987a; Rao et al., 1987b; Reddy et al., 1987), currently there is no available antibody for detecting ERG in clinical specimens. The ERG protein belongs to a highly homologous group of proteins, the ETS (E-twenty six specific, E26 transformation specific) multi-gene family of transcription factors, which are conserved throughout the metazoans (Turner and Watson, 2008). ETS proteins contain a winged helix-turn-helix DNA binding domain and a pointed (SAM) domain implicated in protein-protein interaction. The high degree of homology between members of this family presents a significant obstacle for raising an antibody against a specific member of this protein family.

Although polyclonal ERG antibodies are commercially available, these antibodies exhibit low affinity for endogenous levels of the ERG protein and high levels of non-specific staining that limit their usefulness, for example, in immunohistochemistry testing. As such, the commercially available polyclonal ERG antibodies are not suitable for detecting ERG proteins in clinical settings (e.g., in a tissue biopsy).

SUMMARY

The present disclosure provides antibodies that bind to human ERG and can be used, for example, in methods of detecting and treating cancers associated with ERG fusion events and/or ERG overexpression, such as prostate cancer. The antibodies exhibit high affinity for human ERG with little to no non-specific staining and thus are suitable for detecting ERG proteins in clinical settings, including tissue biopsies, blood and urine.

One embodiment is directed to a monoclonal antibody that binds to human ERG and, more specifically, to an epitope formed by the following polypeptide sequence: GQTSKMSPRVPQQDWLSQPPARVTI, which corresponds to amino acid residues 42-66 of human ERG3 (SEQ ID NO:1) and is referred to hereinafter as the "ERG 42-66 epitope." In another embodiment, the antibody is a monoclonal antibody that binds to human ERG, wherein the antibody's binding to human ERG3 (SEQ ID NO: 1) is competitively inhibited by a polypeptide that corresponds to amino acid residues 42-66 of human ERG3.

In one embodiment, the antibody is a monoclonal antibody produced by the hybridoma clone 9FY ("9FY antibody"). In another embodiment, the antibody is a monoclonal antibody that binds to the ERG 42-66 epitope and competitively inhibits the binding of the 9FY antibody to human ERG3.

In other embodiments, the monoclonal antibody is humanized, chimerized or fully human. In one aspect, the monoclonal antibody comprises the complementarity determining regions (CDRs) of the light and heavy chain variable regions of a non-human ERG antibody that binds the ERG 42-66 epitope, which are joined to the framework (FR) regions of the light and heavy chain variable regions of a human antibody, and optionally joined to the light and heavy chain constant regions of a human antibody. In one embodiment, the monoclonal antibody binds to the ERG 42-66 epitope and comprises a light chain variable domain comprising the three CDRs in SEQ ID NO:2 and a heavy chain variable domain comprising the three CDRs in SEQ ID NO:3. This humanized antibody retains the ERG antigen specificity of the parental antibody, but is less immunogenic in a human subject.

In another aspect, the antibody is a chimeric monoclonal antibody. The chimeric antibody contains the light and heavy chain variable regions of a non-human ERG antibody that binds the ERG 42-66 epitope, which are optionally joined to the light and heavy chain constant regions of a human antibody. This chimeric antibody retains the ERG antigen specificity of the parental antibody, but is less immunogenic in a human subject. In one embodiment, the monoclonal antibody binds to the ERG3 42-66 epitope and comprises a light chain variable domain comprising the amino acid sequence of SEQ ID NO:2 and a heavy chain variable domain comprising the amino acid sequence of SEQ ID NO:3.

Also contemplated is a fully human ERG antibody that binds to the ERG 42-66 epitope.

The monoclonal antibodies described herein that bind to the ERG 42-66 epitope can be used in a variety of research and medical applications. For example, the disclosure provides compositions comprising any one of the monoclonal antibodies described herein that bind to the ERG 42-66 epitope and their use for detecting or treating cancers or pathologic conditions associated with an ERG fusion event or ERG overexpression, including, for example, prostate cancer, Ewing's sarcoma, acute myeloid leukemia, megakaryoblastic leukemia, endothelial cancer, and acute T-lymphoblastic leukemia. Monoclonal antibodies that bind to the ERG 42-66 epitope can also be used to detect human ERG or a fusion protein comprising all or part of a human ERG polypeptide, such as an ERG protein encoded by a TMPRSS2/ERG fusion transcript, in a biological sample.

Another aspect is related to compositions comprising the ERG 42-66 polypeptide. In one embodiment, the composition further comprises an adjuvant and/or a hapten, such as KLH, coupled to the ERG 42-66 polypeptide. These compositions can be used, for example, in a method of producing antibodies. In one embodiment, the method comprises administering the composition to a non-human mammal, including but not limited to a mouse or rabbit. The method may further comprise isolating B cells from the non-human mammal, immortalizing the B cells to create a cell line capable of producing a monoclonal antibody, and selecting the monoclonal antibody that binds to the ERG 42-66 epitope.

In a further aspect, the invention provides isolated polynucleotides that comprise nucleic acid sequences encoding the amino acid sequences of one or more of the CDRs of the light and/or heavy chain variable regions of a monoclonal antibody described herein that binds to the ERG 42-66 epitope, including, for example, the 9FY antibody. Similarly, the invention provides isolated polynucleotides that comprise DNA sequences encoding the amino acid sequence of the light and/or heavy chain variable regions of a monoclonal antibody described herein that binds to the ERG 42-66 epitope, including, for example, the 9FY antibody.

BRIEF DESCRIPTION OF THE DRAWINGS

The accompanying drawings, which are incorporated in and constitute a part of this specification, illustrate certain embodiments, and together with the written description, serve to explain certain principles of the antibodies and methods disclosed herein.

FIGS. 4A-E show that the 9FY antibody specifically recognizes endogenous ERG protein in an immunofluorescence (IF) assay. ERG is stained by primary 9FY antibody followed by goat anti-mouse ALEXA FLUOR® 594 (Invitrogen, Carlsbad, Calif.) secondary antibody (red). The androgen inducible PSA that is negatively controlled by ERG is stained by primary rabbit polyclonal anti-PSA followed by goat anti-rabbit ALEXA FLUOR® 488 (Invitrogen, Carlsbad, Calif.) secondary antibody (green). DNA is stained by DAPI (blue). Merged images in the right columns show nuclear localization of ERG. FIG. 4A shows that ERG knockdown with ERG siRNA eliminates ERG and nuclear 9FY antibody staining from R1881 treated VCaP cells. Cytoplasmic PSA expression is consistent with the hormone induction of VCaP cells. FIG. 4B shows that the immunizing polypeptide (Competing peptide) eliminates ERG staining with 9FY antibody. In contrast, a control polypeptide (Non-competing peptide) does not affect 9FY antibody staining. FIG. 4C shows that the 9FY antibody detects the robust activation of ERG expression in response to androgen hormone (R1881) in TMPRSS2/ERG fusion harboring VCaP cells but not in LNCaP cells that do not express endogenous ERG. FIG. 4D shows that 9FY antibody staining is reduced in VCaP cells in response to ERG knockdown with ERG siRNA. PSA expression is increased in response to ERG knockdown that is consistent with the negative regulatory role of ERG on the expression of PSA. 9FY antibody detects ERG even in the 1:5,000 to 1:20,000 fold dilution ranges of the 9FY antibody stock solution of 3.7 mg/ml. FIG. 4E shows that performing an IF assay in the absence of 9FY antibody and in the presence of the secondary antibody yields no background staining.

FIG. 5A shows representative view fields of prostate sections stained with 9FY antibody. Superior distinction between prostate tumor epithelium and benign epithelium is evident in IHC. The lack of staining of prostatic stroma is also evident. Vascular endothelia that express wild-type ERG are stained by 9FY antibody and present an excellent internal reference for the proper function of 9FY antibody. FIG. 5B shows a high magnification view of an FFPE section and the clear staining of prostate tumor epithelium by the 9FY antibody. FIG. 5C shows the panoramic view of ERG staining by 9FY antibody on a section of formalin fixed paraffin embedded (FFPE) human prostate radical prostatectomy specimen. FIG. 5D shows the corresponding hematoxylin and eosin staining of the section.

FIGS. 14A and 14C show 9FY antibody staining in wild type and ERG transgenic prostate tissue, respectively. Solid arrows mark prostate glands and dashed arrows indicate endothelial cells. FIGS. 14B and 14D show the staining patterns of the commercially available C20 (sc 353) antibody in wild type and ERG transgenic prostate tissue, respectively.

Figures 1A, 1B:
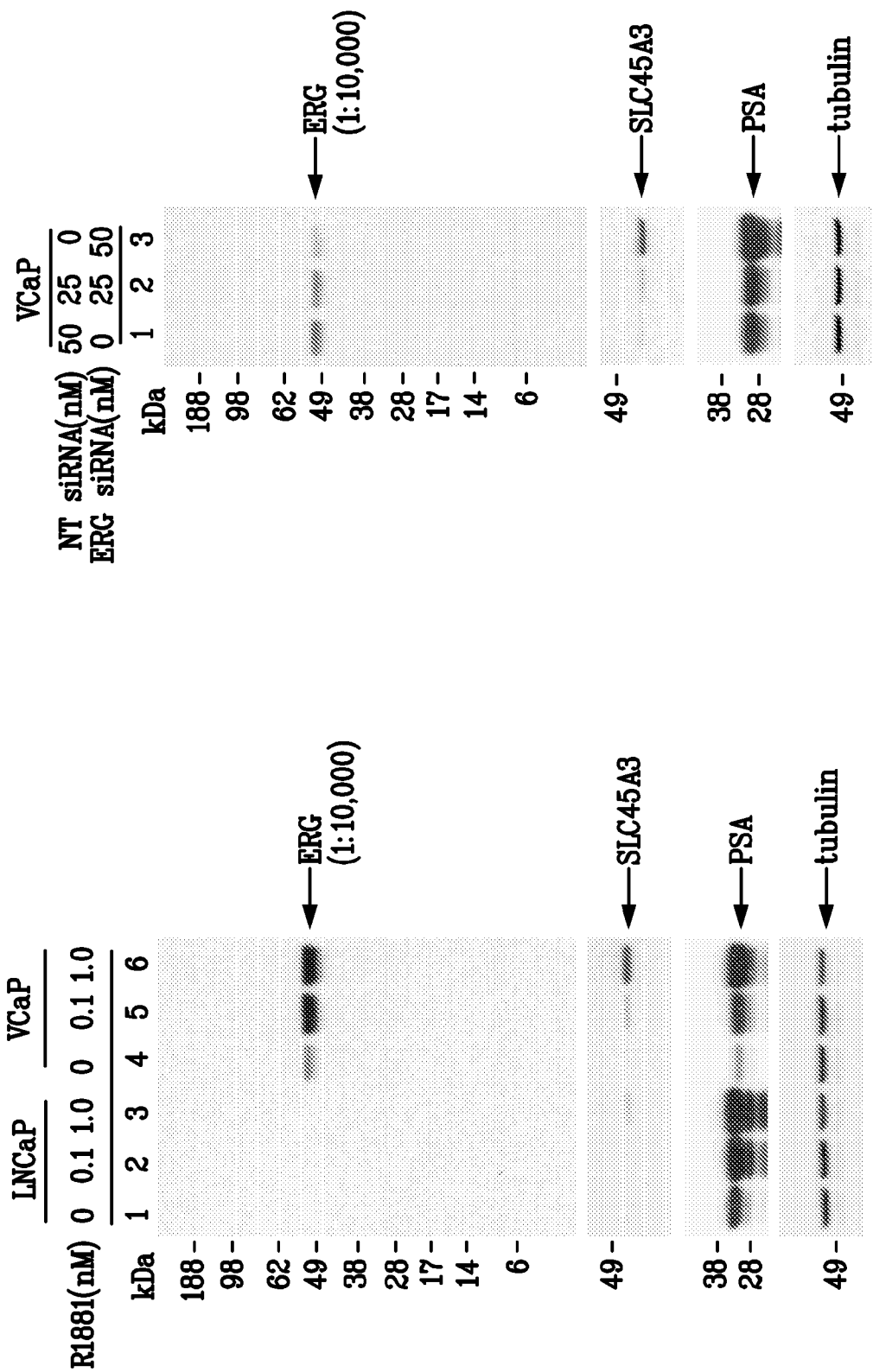
FIG. 1A shows that the 9FY antibody detects the endogenous ERG protein encoded by the TMPRSS2/ERG3 fusion transcript (50-52 kDa) in immunoblots of TMPRSS2/ERG3 fusion harboring VCaP cells, expressed in response to synthetic androgen hormone (R1881) treatment (lanes 4-6). 9FY antibody does not show immuno-reactivity to LNCaP cells that do not harbor a TMPRSS2/ERG fusion protein (lanes 1-3). On the bottom panels, hormone dose dependent expression of prostein (SLC45A3) and PSA (KLK3) are shown.
FIG. 1B shows that ERG siRNA inhibits ERG expression in R1881 treated VCaP cells.

Hollow triangles indicate specimens with no ERG oncoprotein or with non-detectable TMPRSS2-ERG fusion transcript.

DETAILED DESCRIPTION

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-inding); a $F(ab')_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide may be used as a linker, but other linkers are known in the art. These antibody fragments are obtained using conventional techniques known to those with skill in the art, and the fragments are evaluated for function in the same manner as are intact antibodies.

The term "effective amount" refers to a dosage or amount that is sufficient to reduce the activity of ERG or a fusion protein comprising all or part of a human ERG polypeptide, such as an ERG protein encoded by a TMPRSS2/ERG fusion transcript, to result in amelioration of symptoms in a patient or to achieve a desired biological outcome. For example, with prostate cancer the desired biological outcome may include a decrease in tumor size, a decrease in Gleason score, and/or increased tumor differentiation.

The term "ERG protein encoded by a TMPRSS2/ERG fusion transcript" refers to a truncated ERG protein, such as ERG3, encoded by a transcript generated by a fusion event between a TMPRSS2 gene promoter and a human ERG transcript.

The term "fusion protein" refers to a protein translated from a transcript generated from a fusion event between two nucleotide sequences. One of the nucleotide sequences may be a non-coding sequence (e.g., a TMPRSS2, SLC45A3, or NDRG1 sequence) while the other nucleotide sequence represents all or part of a coding a sequence (e.g., ERG). Alternatively the two nucleotide sequences may both be coding sequences.

The term "human antibody" includes antibodies having variable and constant regions corresponding substantially to human germline immunoglobulin sequences known in the art, including, for example, those described by Kabat et al. (See Kabat, et al. (1991) Sequences of Proteins of Immunological Interest, Fifth Edition, U.S. Department of Health and Human Services, NIH Publication No. 91-3242), which is hereby incorporated by reference in its entirety. Human antibodies may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The terms "treatment" or "treating" and the like refer to any treatment of any disease or condition in a mammal, e.g. particularly a human or a mouse, and includes inhibiting a disease, condition, or symptom of a disease or condition, e.g., arresting its development and/or delaying its onset or manifestation in the patient or relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art.

The term "isolated," when used in the context of an antibody, refers to an antibody that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The term "9FY antibody" is a monoclonal antibody produced by the hybridoma clone named 9FY that has been maintained through successive cell culture passages in the laboratory at the Center for Prostate Disease Research in Rockville, Md. since Sep. 17, 2008. Aliquots of the 9FY hybridoma clone have also been labeled, frozen, and stored at the Center for Prostate Disease Research.

The term "ERG 42-66 epitope" refers to a conformational or linear epitope formed by amino acid residues 42-66 of SEQ ID NO: 1.

The term "ERG 42-66 polypeptide" refers to a polypeptide having no more than 60 amino acid residues, wherein the polypeptide includes amino acid residues 42-66 of SEQ ID NO: 1. In certain embodiments, the ERG 42-66 polypeptide has no more than 50, 40, 30, or 25 amino acid residues.

The term "human ERG3" refers to a polypeptide having the amino acid sequence of ACCESSION NP_891548; VERSION NP_891548.1 GI:33667107:

```
                                                  (SEQ ID NO: 1)
   1  mastikeals  vvsedqslfe  caygtphlak  temtassssd ygqtskmspr  vpqqdwlsqp 61  parvtikmec  npsqvngsrn  spdecsvakg  gkmvgspdtv gmnygsymee  khmpppnmtt 121  nerrvivpad  ptlwstdhvr  qwlewavkey  glpdvnillf qnidgkelck  mtkddfqrlt 181  psynadills  hlhylretpl  phltsddvdk  alqnsprlmh arntggaafi  fpntsvypea 241  tqrittrpdl  pyepprrsaw  tghghptpqs  kaaqpspstv pktedqrpql  dpyqilgpts 301  srlanpgsgq  iqlwqfllel  lsdssnssci  twegtngefk mtdpdevarr  wgerkskpnm 361  nydklsralr  yyydknimtk  vhgkryaykf  dfhgiaqalq phppesslyk  ypsdlpymgs 421  yhahpqkmnf  vaphppalpv  tsssffaapn  pywnsptggi ypntrlptsh  mpshlgtyy
```

2. Anti-ERG Antibodies

As discussed above, ERG is a proto-oncogene that belongs to the ETS family of transcription factors. Because of high degree of homology among members of the ETS family of proteins, raising an antibody against a specific member of the family remains a challenge. Furthermore, to date, polyclonal antibodies raised against ERG retain significant non-specific binding, preventing such antibodies from being used in a clinical setting (e.g., IHC) to aid in the detection of cancerous cells or tissue expressing ERG or fusion proteins comprising all or part of an ERG polypeptide, such as an ERG polypeptide encoded by a TMPRSS2/ERG, SLC45A3/ERG, or NDRG1/ERG fusion transcript that have been identified in prostate cancers.

This disclosure provides antibodies that bind to human ERG. More specifically, the antibodies bind to the ERG 42-66 epitope. Amino acids 42-66 of human ERG3 are encoded by a nucleotide sequence that maps to exon 8 of the ERG locus (Owczarek et al., 2004). Exon 8 is found in ERG2, ERG3, ERG4, ERG5 (partial exon), ERG7, and ERG8 but not in ERG1 (Owczarek et al., 2004). Thus, the antibodies disclosed herein do not cross react with ERG1 protein.

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain ($V_L$) and a constant (C) domain ($C_L$). Each heavy chain includes an N-terminal V domain (VH), three or four C domains (CHs), and a hinge region. The CH domain most proximal to VH is designated as CHI. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. Identification and numbering of framework and CDR residues is as described by Chothia et al., Structural determinants in the sequences of immunoglobulin variable domain, J Mol Biol 1998, 278:457-79, which is hereby incorporated by reference in its entirety.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual. Cold Spring Harbor Laboratory*, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of Proteins of Immunological Interest. US Department of Health and Human Services* (1991), eds. Kabat et al. Another standard for characterizing the antigen binding site is to refer to the hypervariable loops as described by Chothia. See. e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains. In: Antibody Engineering Lab Manual* (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

In one embodiment, the antibody is a monoclonal antibody that binds to the ERG 42-66 epitope and is produced by the hybridoma clone 9FY ("9FY antibody"). The light chain variable domain of the 9FY antibody comprises the amino acid sequence of SEQ ID NO:2. The amino acid sequences of the CDR1, CDR2, and CDR3 of the light chain variable domain of the 9FY antibody correspond to SSVYY (SEQ ID NO:4), YTS, and LQFSTSPWT (SEQ ID NO:5), respectively. The heavy chain variable domain of the 9FY antibody comprises the amino acid sequence of SEQ ID NO:3. The amino acid sequences of the CDR1, CDR2, and CDR3 of the heavy chain variable domain of the 9FY antibody correspond to GYTFTNYG (SEQ ID NO:6), IDTYTGEP (SEQ ID NO:7), and VRKRAYDYEIY (SEQ ID NO:8), respectively.

In another embodiment, the antibody is a monoclonal antibody that binds to the ERG 42-66 epitope and competitively inhibits the binding of the 9FY antibody to human ERG3. In yet another embodiment, the antibody is a monoclonal antibody that binds to the ERG 42-66 epitope and competitively inhibits the binding of an antibody, having a variable light chain comprising the amino acid sequence of SEQ ID NO:2 and a variable heavy chain comprising the amino acid sequence of SEQ ID NO:3, to human ERG3. Whether an antibody competitively inhibits the binding of an antibody to a protein, such as human ERG3, can be assessed using routine methods in the art, including, for example, the methods described in the examples of this application.

Antibodies, in which CDR sequences or heavy or light chain variable domains differ only insubstantially from those of the 9FY antibody are also contemplated. Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody.

In certain embodiments, a monoclonal antibody binds to the ERG 42-66 epitope and comprises a heavy chain that is at least about 70%, at least about 80%, at least about 90%, at least about 95% or at least about 98% identical to the amino acid sequence of the heavy chain variable domain of the 9FY antibody, and a light chain that is at least about 70%, at least about 80%, at least about 90%, at least about 95% or at least about 98% identical to the amino acid sequence of the light chain variable domain of the 9FY antibody. In other embodiments, a monoclonal antibody binds to the ERG 42-66 epitope and has six CDRs (H1, H2, H3, L1, L2, and L3) that are at least about 70%, at least about 80%, at least about 90%, at least about 95% or at least about 98% identical to the six CDRs (H1, H2, H3, L1, L2, and L3) of the heavy and light chain sequences of the 9FY antibody. In one embodiment, the monoclonal antibody binds to the ERG 42-66 epitope and comprises a light chain variable domain identical to SEQ ID NO:2 except for 1, up to 2, up to 3, up to 4, up to 5, up to 6, up to 7, and in certain cases, up to 10 amino acid substitutions in the CDR sequences. In another embodiment, the monoclonal antibody binds to the ERG 42-66 epitope and comprises a heavy chain variable domain identical to SEQ ID NO:3 except for 1, up to 2, up to 3, up to 4, up to 5, up to 6, up to 7, and in certain cases, up to 10 amino acid substitutions in the CDR sequences. The specific amino acid positions that can be substituted in a CDR, as well as the donor amino acid that can be substituted into those positions can be readily determined by one of skill in the art using known methods, such as those disclosed in published U.S. Application 2006/0099204, the disclosure of which is hereby incorporated by reference in its entirety.

In certain embodiments, the monoclonal antibody is a humanized antibody that binds to the ERG 42-66 epitope and comprises (a) a light chain variable domain comprising the CDR1, CDR2, and CDR3 sequences of SEQ ID NO:2; (b) a heavy chain variable domain comprising the CDR1, CDR2, and CDR3 sequences of SEQ ID NO:3; and (c) the framework regions of the light and heavy chain variable regions of a human antibody. The humanized antibody optionally further comprises light and heavy chain constant regions of at least one human antibody.

In another embodiment, the monoclonal antibody is a chimeric antibody that binds to the ERG 42-66 epitope and comprises a light chain variable domain comprising the amino acid sequence of SEQ ID NO:2 and a heavy chain variable domain comprising the amino acid sequence of SEQ ID NO:3. The chimeric antibody optionally further comprises light and heavy chain constant regions of at least one human antibody. In another embodiment, the monoclonal antibody is a human antibody that binds to the ERG 42-66 epitope.

In certain embodiments, the monoclonal antibody that binds to the ERG 42-66 epitope has a dissociation constant ($K_D$) of about 280 nM or less. In other embodiments, the monoclonal antibody that binds to the ERG 42-66 epitope detects ERG expressing carcinoma with a specificity of greater than 99%. In other embodiments, the monoclonal antibody that binds to the ERG 42-66 epitope does not cross react with the human FLi1 protein. Cross reactivity can be measured using routine methods in the art, including, for example, a Western blot.

The antibodies provided in this disclosure that bind to the ERG 42-66 epitope are optionally isolated.

It may also be desirable to modify the antibodies of the present invention to improve effector function, e.g., so as to enhance antigen-dependent cell-mediated cytotoxicity (ADCC) and/or complement dependent cytotoxicity (CDC) of the antagonist. One or more amino acid substitutions or the introduction of cysteine in the Fc region may be made, thereby improving internalization capability and/or increased complement-mediated cell killing and ADCC. See Caron et al., J. Ex. Med. 176:1191-1195 (1991) and Shopes, B. J. Immunol. 148:2918-2022 (1992), incorporated herein by reference in their entirety. An antibody fusion protein may be prepared that has dual Fc regions with both enhanced complement lysis and ADCC capabilities. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., *Immunomethods* 4:25-34, 1994; and de Haas et al., *J. Lab. Clin. Med.* 126:330-41, 1995).

3. Nucleic Acids, Cloning and Expression Systems

The present disclosure further provides isolated nucleic acids encoding the disclosed antibodies or portions thereof. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein encode at least one CDR (H1, H2, H3, L1, L2, and/or L3), a $V_L$ domain (SEQ ID NO:2), and/or a $V_H$ domain (SEQ ID NO:3) of the 9FY antibody.

The present disclosure also provides constructs in the form of plasmids, vectors, phagemids, transcription or expression cassettes which comprise at least one nucleic acid encoding a CDR, a $V_H$ domain, and/or a $V_L$ domain of the 9FY antibody. The disclosure further provides a host cell which comprises one or more constructs as above.

Also provided are methods of making the polypeptides encoded by these nucleic acids. The method comprises expressing the encoded polypeptide from the encoding nucleic acid. Expression may be achieved by culturing under appropriate conditions recombinant host cells containing the nucleic acid. Following production by expression a $V_H$ or $V_L$ domain, or specific binding member may be isolated and/or purified using any suitable technique, then used as appropriate.

Systems for cloning and expression of a polypeptide in a variety of different host cells are well known in the art. For cells suitable for producing antibodies, see Gene Expression Systems, Academic Press, eds. Fernandez et al., 1999. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate.

A further aspect of the disclosure provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

4. Methods of Making Antibodies

Numerous methods known to those skilled in the art are available for obtaining antibodies or antigen-binding fragments thereof. For example, antibodies can be produced using recombinant DNA methods. See, e.g., U.S. Pat. No. 4,816,567, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference in their entirety.

Monoclonal antibodies may also be produced by preparing immortalized cell lines capable of producing antibodies having desired specificity. Such immortalized cell lines may be produced in a variety of ways. Conveniently, a small vertebrate, such as a mouse, is hyperimmunized with the desired immunogen. The vertebrate is then sacrificed, usually several days after the final immunization, the spleen cells removed, and the spleen cells immortalized. The most common technique is fusion with a myeloma cell fusion partner, as first described by Kohler and Milstein (1975) Nature 256:495-497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in Antibodies: A Laboratory Manual, Harlow and Lane, eds., Cold Spring Harbor Laboratory, 1988, the full disclosure of which is incorporated herein by reference.

Immortalized cell lines can be screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597 WO 92/18619; WO 91/17271; WO 92/20791; WO 92/15679; WO 93/01288; WO 92/01047; WO 92/09690; and WO 90/02809, the disclosures of which are incorporated herein by reference in their entirety.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See. e.g., XENOMOUSE™, Green et al. (1994) Nature Genetics 7:13-21, US 2003-0070185, WO 96/34096, published Oct. 31, 1996, and PCT Application No. PCT/US96/05928, filed Apr. 29, 1996, the disclosures of which are incorporated herein by reference in their entirety.

In another embodiment, a monoclonal antibody is obtained from the non-human animal, and then modified. For example, humanized, deimmunized, and chimeric antibodies may be produced using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B, the disclosures of which are incorporated herein by reference in their entirety. Humanizing an antibody involves transplanting the combining-site of a nonhuman antibody onto a human antibody. This may be performed by grafting the nonhuman CDRs onto human framework and optionally human constant regions or by transplanting the entire nonhuman variable domains but hiding them with a human-like surface by replacement of certain exposed residues. Details on creating a humanized antibody are disclosed in U.S. Pat. No. 5,472,693, which is hereby incorporated by reference.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539, the disclosure of which is incorporated herein by reference in its entirety). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. Nos. 5,585,089; 5,693,761; 5,693,762; 5,859,205; and 6,407,213, the disclosures of which are incorporated herein by reference in their entirety. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80: 7308-7312, 1983; Kozbor et al., *Immunology Today*, 4: 7279, 1983; Olsson et al., *Meth. Enzymol.*, 92: 3-16, 1982), the disclosures of which are incorporated herein by reference in their entirety, and may be made according to the teachings of PCT Publication WO92/06193 or EP 0239400, the disclosures of which are incorporated herein by reference in their entirety. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638, the disclosures of which are incorporated herein by reference in their entirety. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064, the disclosure of which is incorporated herein by reference in its entirety.

Human antibodies can be generated using methods known in the art, such as phage display technology. Phage display technology mimics the mammalian immune system by cloning large libraries of antibody genes and selecting for binding to a desired target, such as the ERG 42-66 epitope. The libraries used in phage display technology can be made from several sources. For example, an immune library, created from humans exposed to a desired antigen through vaccination or disease, has high levels of circulating antibodies to the antigen even when the library is relatively small. As another example, a naïve library, made from mRNA isolated from non-immunized individuals, can be used repeatedly to isolate antibodies against a variety of antigens. As still another example, a synthetic library, in which germline antibody gene segments are cloned and arranged combinatorially in vitro to reconstitute genes encoding complete $V_H$ and $V_L$ chains, has the advantage of producing antibodies with specificity to self-antigens. Semi-synthetic libraries can also be made by selecting one or more antibody frameworks and randomizing sequences within the CDR loops.

In phage display technology, once a library is created, it is fused to a surface protein of phages, commonly pIII. In a process known as panning, phages displaying an antibody specific for the antigen of interest are enriched by selective adsorption onto immobilized antigen. Subsequently, the bound phage can be eluted from the surface and amplified through infection of *E. coli* cells.

Other modifications of phage display technology to generate human antibodies are also known in the art. For example, antibodies can be displayed on the surfaces of microbial cells, such as *E. coli* and *Saccharomyces cerevisiae*, instead of on the surface of bacteriophages. In this case, screening can be performed by incubation with a fluorescently tagged ligand in buffer. Cells that display the antibodies that bind to the ligand become fluorescently labeled and are isolated by fluorescence-activated cell sorting. Another modification, termed ribosome display, relies on the formation of a ternary complex between ribosomes, mRNA, and the polypeptide.

Another method known in the art to produce human antibodies is one that uses transgenic mice. The native immunoglobulin repertoire in these mice has been replaced with human V-genes in the murine chromosome. The mice can be injected with a desired antigen and the resulting antibodies can be recovered by cloning and screening an immune library, or by conventional hybridoma technology. These mice produce significant levels of fully human antibodies that only differ in glycosylation patterns.

The anti-ERG antibodies described herein can be derivatized or linked to another functional molecule (such as another peptide or protein (e.g., a Fab fragment)). For example, the antibody can be functionally linked (e.g., by chemical coupling, genetic fusion, non-covalent association or otherwise) to at least one other molecular entity, such as another antibody (e.g., a bispecific or a multispecific antibody), toxin, radioisotope, cytotoxic or cytostatic agent, among others.

5. Methods of Use

The monoclonal antibodies described herein that bind to the ERG 42-66 epitope can be used in a variety of research and medical applications. In one aspect, the disclosure provides a method of treating a malignancy or disease in a subject, comprising administering to said subject a therapeutically effective amount of a monoclonal antibody described herein that binds to the ERG 42-66 epitope formulated in a pharmaceutically acceptable vehicle, wherein the malignancy or disease is caused by an ERG fusion event (e.g., fusion between a TMPRSS2, SLC45A3, or NDRG1 gene promoter sequence and an ERG gene sequence or between a first gene sequence and an ERG gene sequence) and/or ERG overexpression. In one embodiment, the malignancy or disease is prostate cancer, Ewing's sarcoma, acute myeloid leukemia, acute T-lymphoblastic leukemia, megakaryoblastic leukemia, colon cancer, or a disease of the endothelial cells, such as endothelial cancer. In another embodiment, the disease is Alzheimer's disease or Down's syndrome.

In addition, the monoclonal antibodies described herein that bind to the ERG 42-66 epitope can be used to detect ERG proteins, including fusion proteins comprising all or part of an ERG polypeptide, such as an ERG protein encoded by a TMPRSS2/ERG, SLC45A3/ERG, or NDRG1/ERG fusion transcript, in a biological sample. In one embodiment, the method comprises contacting the monoclonal antibody described herein that binds to the ERG 42-66 epitope with the biological sample and analyzing the biological sample to detect binding of the monoclonal antibody to human ERG or the fusion protein in the biological sample. In one embodiment, the ERG polypeptide is ERG3. In another embodiment, the ERG protein encoded by the TMPRSS2/ERG or SLC45A3/ERG fusion transcript is a truncated ERG3 protein. In one embodiment, the biological sample comprises a tissue or a cell, such as a prostate tissue or a prostate cell. In other embodiments, the biological sample comprises a biological fluid, such as urine or blood, wherein the biological fluid contains cancer cells, such as prostate cancer cells. In other embodiments, the biological fluid is blood, serum, urine, saliva, sputum, or stool.

In another embodiment, the disclosure provides a method for detecting cancer or a disease in a patient, the method comprising contacting a monoclonal antibody described herein that binds to the ERG 42-66 epitope with a biological sample obtained from the patient and analyzing the biological sample, wherein binding of the antibody to cells in the biological sample indicates the presence of cancer in the biological sample. In one embodiment, the cancer is prostate cancer. In another embodiment, the cancer is Ewing sarcoma, acute myeloid leukemia, acute T-lymphoblastic leukemia, megakaryoblastic leukemia, colon cancer, or endothelial cancer. In one embodiment, the biological sample comprises a tissue or a cell, such as a prostate tissue or a prostate cell. In other embodiments, the biological sample comprises a biological fluid, such as urine or blood, wherein the biological fluid contains cancer cells, such as prostate cancer cells. In other embodiments, the biological fluid is blood, serum, urine, saliva, sputum, or stool. In one embodiment, the cancer or disease is associated with an ERG fusion event (e.g., fusion between a TMPRSS2, SLC45A3, or NDRG1 gene promoter sequence and an ERG gene sequence) and/or ERG over expression. The binding of the antibody to hematopoietic cells or endothelial cells in blood vessels or capillaries is normal and typically does not indicate the presence of cancer. However the detection of an ERG protein, including fusion proteins comprising all or part of an ERG polypeptide, in any cell other than a normal hematopoietic cell or a normal endothelial cell in blood vessels or capillaries indicates the presence of cancer in the sample.

Also, as shown in the examples, the anti-ERG antibodies described herein can be used to detect ERG-positive PIN. Patients exhibiting ERG-positive prostatic intraepithelial neoplasia (PIN) likely also have ERG-positive prostate cancer or are at high risk for developing ERG-positive prostate cancer. Thus, if ERG-positive PIN, but not ERG-positive prostate cancer, is detected in a patient, the patient should undergo additional biopsies or more frequent biopsies to monitor the development of prostate cancer in the patient. Accordingly, the anti-ERG antibodies described herein can be used to inform decisions about whether to perform additional biopsies or the frequency of future biopsies.

In yet another aspect, the monoclonal antibodies described herein that bind to the ERG 42-66 epitope can be used to monitor the efficacy of therapeutic regimens. Thus, one embodiment is directed to a method of monitoring hormone ablation therapy, the method comprising contacting a monoclonal antibody described herein that binds to the ERG 42-66 epitope with a biological sample obtained from a patient who has received hormonal ablation therapy, and measuring the expression of human ERG or a fusion protein comprising all or part of a human ERG polypeptide in the biological sample, wherein reduced ERG expression following androgen ablation therapy indicates the hormone ablation therapy was effective and correlates with an increased survival time. The level of ERG expression in the patient after hormonal ablation therapy can be compared to the level of ERG expression in the same patient before commencing hormonal ablation therapy or can be compared to a standardized control value, representing a heightened level of ERG expression.

Also provided is a method for identifying a nucleic acid sequence, such as a promoter sequence, or a polypeptide that interacts with an ERG polypeptide. Nucleic acids and/or proteins identified by such methods may define new therapeutic targets in the ERG network. In one embodiment, the method comprises incubating a sample comprising a nucleic acid molecule or a polypeptide with an ERG polypeptide, incubating the sample and the ERG polypeptide with an antibody that binds to the 42-66 ERG epitope, and determining whether a complex forms between the nucleic acid molecule and the ERG polypeptide or between the polypeptide and the ERG polypeptide, wherein detecting the formation of a complex with the antibody indicates that the nucleic acid molecule or polypeptide interacts with the ERG polypeptide. Such methods can be carried out using techniques that are conventional in the art, including, for example, immunoprecipitation assays.

Any appropriate label may be used in the methods and compositions described herein. A label is any molecule or composition bound to an analyte, analyte analog, detector reagent, or binding partner (e.g., antibody) that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, haptens (e.g., biotin, digoxigenin (DIG), dintrophenol (DNP), etc.), radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulphur particles, protein-adsorbed tellurium particles, protein-adsorbed carbon particles, and protein-coupled dye sacs. The attachment of a compound to a label can be through any means, including covalent bonds, adsorption processes, hydrophobic and/or electrostatic bonds, as in chelates and the like, or combinations of these bonds and interactions and/or may involve a linking group.

Some labels, such as haptens, are typically coupled with detection reagents for colorimetric detection. For example, biotin can be coupled to a streptavidin-HRP compound that is colorimetrically detected using DAB. Those skilled in the art will appreciate the myriad label and detection options which find utility as detection reagents useful in compositions and methods of the present invention.

In some embodiments, a molecule, such as an antibody (e.g., monoclonal antibody), is detected directly by conjugation with a detectable moiety. For example, monoclonal antibodies as described herein can be directly conjugated to a detectable moiety, such as a fluorescent compound (including fluorescein, fluorescein isothiocyanate (FITC), rhodamine, 5-dimethylamine-1-napthalenesulfonyl chloride, phycoerythrin, lanthanide phosphors, ALEXA FLUOR® (Invitrogen, Carlsbad, Calif.) dyes, or the cyanine family of dyes (such as Cy-3 or Cy-5) and the like); a bioluminescent compound (such as luciferase, green fluorescent protein (GFP), yellow fluorescent protein, etc.); an enzyme that produces a detectable reaction product (such as horseradish peroxidase, β-galactosidase, luciferase, alkaline phosphatase, or glucose oxidase and the like), or a radiolabel (such as $^3$H, $^{14}$C, $^{15}$N, $^{35}$S, $^{90}$Y, $^{99}$Tc, $^{111}$In, $^{125}$I, or $^{131}$I).

In some embodiments, a molecule, such as an antibody (e.g., monoclonal antibody), is indirectly detected. For example, secondary antibodies are raised against primary antibodies (e.g., a monoclonal ERG antibody as described herein) as known to a skilled artisan, where the secondary antibody is labeled for detection. The secondary antibody is conjugated to a detectable moiety. For example, the secondary antibody can be conjugated to a reporter enzyme such as alkaline phosphatase (AP) or horseradish peroxidase (HRP) for subsequent colorimetric detection. In some embodiments, the secondary antibody is conjugated to a fluorescent moiety as previously described (e.g., FITC, Cy dyes, ALEXA FLUOR® (Invitrogen, Carlsbad, Calif.) dyes, rhodamine, etc.). In some embodiments, a primary monoclonal ERG antibody in indirectly detected with a secondary antibody conjugated to a hapten, such as, biotin DNP, DIG, etc., which is further coupled to a detectable reagent molecule such as streptavidin-HRP, which is subsequently detected colorimetrically by reaction with 3,3'-Diaminobenzidine (DAB). A skilled artisan will appreciate the myriad of enzymatic and luminescent detection methods utilized for visualization of protein-protein interactions as described herein.

6. Formulations and Administration

The disclosure provides compositions comprising a monoclonal antibody described herein that binds to the ERG 42-66 epitope. In certain embodiments, the compositions are suitable for pharmaceutical use and administration to patients. These compositions comprise a monoclonal antibody described herein that binds to the ERG 42-66 epitope and a pharmaceutically acceptable excipient. The compositions may also contain other active compounds providing supplemental, additional, or enhanced therapeutic functions. The pharmaceutical compositions may also be included in a container, pack, or dispenser together with instructions for administration. In one embodiment, the composition comprises a monoclonal antibody described herein that binds to the ERG 42-66 epitope for treatment of a disease, such as Alzheimer's disease, or a malignancy, such as prostate cancer, Ewing's sarcoma, acute myeloid leukemia, acute T-lymphoblastic leukemia, megakaryoblastic leukemia, colon cancer or endothelial cancer.

A pharmaceutical composition of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically contemplated, by such means as depot injections or erodible implants. Localized delivery is particularly contemplated, by such means as delivery via a catheter to one or more arteries, such as the renal artery or a vessel supplying a localized tumor.

In one embodiment a subject antibody is administered to a patient by intravenous, intramuscular or subcutaneous injection. An antibody may be administered within a dose range between about 0.1 mg/kg to about 100 mg/kg; between about 1 mg/kg to 75 mg/kg; or about 10 mg/kg to 50 mg/kg. The antibody may be administered, for example, by bolus injunction or by slow infusion. Slow infusion over a period of 30 minutes to 2 hours may be used.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

7. Kits

In some embodiments, ERG related molecules as described herein (e.g., monoclonal antibody, polypeptide, etc.) are supplied in the form of a kit useful, for example, for performing the methods of the present invention. In one embodiment, an appropriate amount of at least one ERG related molecule (e.g., monoclonal antibody, polypeptide, etc.) is provided in one or more containers. In other embodiments, at least one ERG related molecule (e.g., monoclonal antibody, polypeptide, etc.) is provided suspended in an aqueous solution or as a freeze-dried or lyophilized powder, for instance. The container(s) in which the at least one ERG related molecule (e.g., monoclonal antibody, polypeptide, etc.) is supplied can be any conventional container that is capable of holding the supplied form, for instance, microfuge tubes, ampoules, or bottles. The amount of ERG related molecule (e.g., monoclonal antibody, polypeptide, etc.) supplied can be any appropriate amount.

In other embodiments, control slides upon which are mounted one or more tissue or cell preparations (e.g., biopsy, xenografts, cell pellets, or clotted cells) that may serve as positive and/or negative controls for a ERG related molecule (e.g., monoclonal antibody, polypeptide, etc.) may be provided in an appropriate and separate container.

Other kit embodiments include means for detection of the ERG related molecule, such as secondary antibodies. In some such instances, the secondary antibody is directly labeled with a detectable moiety (as described elsewhere in this disclosure). In other instances, the primary or secondary (or higher-order) antibody is conjugated to a hapten (such as biotin, DNP, DIG, etc.), which is detectable by a detectably labeled cognate hapten-binding molecule (e.g., streptavidin (SA)-horse radish peroxidase, SA-alkaline phosphatase, SA-QDot® (Invitrogen, Carlsbad, Calif.), etc.). In some embodiments, the primary or secondary antibody in conjugated with a fluorescent detection moiety (e.g., FITC, rhodamine, ALEXA FLUOR® (Invitrogen, Carlsbad, Calif.) dyes, Cy designated fluorophores, etc.) Some kit embodiments may include colorimetric reagents (e.g., DAB, AEC, etc.) in suitable containers to be used in concert with primary or secondary (or higher-order) antibodies that are labeled with enzymes for the development of such colorimetric reagents.

In one embodiment, a kit includes instructional materials disclosing methods of use of the kit contents (e.g., ERG related molecule) in a disclosed method. The instructional materials may be provided in any number of forms, including, but not limited to, written form (e.g., hardcopy paper, etc.), in an electronic form (e.g., computer diskette or compact disk) or may be visual (e.g., video files). The kits may also include additional components to facilitate the particular application for which the kit is designed. Thus, for example, the kits may additionally include buffers and other reagents routinely used for the practice of a particular method. Such kits and appropriate contents are well known to those of skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. 9FY Antibody Generation

The hybridoma clone 9FY was obtained by immunizing Balb/C mice with a chemically synthesized polypeptide having amino acids 42-66 of SEQ ID NO: 1 and a cysteine residue added at either the N- or C-terminus to keep the —COOH free (unconjugated). The immunizing polypeptide was conjugated to keyhole limpet hemocyanin (KLH) and injected into the mice with an adjuvant at three separate injection sites at three week intervals. The first injection used Freund's complete as the adjuvant. The second and third injection used Freund's incomplete adjuvant. Serum bleeds were assessed for binding to the immunizing polypeptide using a direct ELISA screen. Mice with the highest titer were chosen for the first hybridoma fusion step. Eight positives clones were confirmed by ELISA and supernatants were analyzed by immunoblot assays using ERG3 protein heterologously expressed in HEK-293 cells. Two of the clones were found to be positive in the immunoblot assay. One of the negative clones from the secondary screen was retained as the negative control. The two positive clones and the negative control were further processed for secondary cloning. One of the positive clones (9FY) that initially showed the strongest positive activity survived the second cloning step. The 9FY clone was grown and injected into 10 mice for ascites production. Ascites was produced and the 9FY antibody was purified over a Protein G column. The 9FY antibody sub-type was determined to be IgG from the purified fraction.

Example 2. 9FY Antibody Specifically Recognizes ERG Protein in Prostate Cancer Cells VCaP cells (Korenchuck et al., 2001, In Vivo, 15:163-68) are a human prostate cancer cell line that over express a TMPRSS2/ERG fusion frequently detected in human prostate tumors. In VCaP cells, endogenous ERG gene transcription is controlled by the androgen inducible TMPRSS2 promoter. LNCaP cells are a human prostate cancer cell line that do not harbor a TMPRSS2/ERG fusion and do not express detectable levels of ERG.

1. Western Blots

LNCaP (ATCC #CRL-1740) and VCaP cells (ATCC, #CRL-2876) were grown in RPMI-1640 (ATCC; #30-2001) and DMEM medium (ATCC; #30-2002), respectively, supplemented with 10% fetal bovine serum (ATCC; #30-2020) and 2 mM glutamine. LNCaP and VCaP cells ($2 \times 10^6$) were seeded onto 10 cm dishes and maintained for five days and three days, respectively, in media with 10% charcoal-stripped fetal bovine serum (c-FBS; #100119 Gemini Bio-Products, Calabasas, Calif.). For androgen induction, the cells were subsequently grown in fresh media with c-FBS supplemented with 0.1 nM R1881 or 1 nM R1881 for another 48 hours. Cells were harvested and analyzed by Western blots and microscopy.

In Western blot experiments, the 9FY antibody recognizes full length protein products (approximately 50-52 kDa) encoded by TMPRSS2/ERG2 and TMPRSS2/ERG3 in response to androgen (R1881) induction (FIG. 1A). The 9FY antibody did not recognize ERG in LNCaP cells, which do not harbor a TMPRSS2/ERG fusion transcript.

To evaluate the specificity of the 9FY antibody recognition, synthetic androgen (R1881) induced VCaP cells and LNCaP cells were transfected with ERG-specific small inhibitory RNA (ERG siRNA) (Sun et al., 2008) and/or a non-targeting ("NT"), control oligonucleotide. The ERG siRNA is targeted to a 19 base pair region in exon 11 and is predicted to inhibit all known ERG splice variants in prostate cells (Sun et al., 2008). Tubulin was used as a loading control in the immunoblot assay.

VCaP cell lysates were prepared in M-PER® mammalian protein extraction reagent (Cat #78501, Thermo, Rockford, Ill.) supplemented with protease and phosphatase inhibitor cocktails (Cat #P2850 & P5726, Sigma, St. Louis, Mo.), from VCaP cells transfected with NT or ERG siRNA oligonucleotides (Dharmacon, Lafayette, Colo.) and incubated for four days. Cells were transfected with 50 nM NT oligonucleotides, 25 nM NT and 25 nM ERG siRNA oligonucleotides or 50 nM ERG siRNA oligonucleotides (lane 3). 25 jtg of cell lysates were loaded in each lane, separated on NUPAGE® SDS gel (Cat #NP0335, Invitrogen, Carlsbad, Calif.), transferred onto PVDF membranes and Western blotted with 1:10,000 9FY antibody. Identical gels were transferred onto PVDF membranes (Cat #LC2005, Invitrogen, Carlsbad, Calif.) and probed with 1:1,000 anti-SLC45A3 antibody (Cat M361529-2), 1:3,000 anti-PSA antibody (Cat #A056201-2, both from DAKO, Carpinteria, Calif.) and 1:1000 anti-alpha-tubulin (Cat #Sc-5286, Santa Cruz, Calif.).

LNCaP cell lysates were prepared from cells that have been grown in RPMI1640 supplemented with 10% charcoal stripped serum for five days and maintained further in fresh R1881 free medium or stimulated with 0.1 nM or 1 nM R1881 for 48 hours. Similarly, VCaP cell lysates were prepared from cells that have been grown in DMEM supplemented with charcoal stripped serum for three days and maintained further in fresh R1881 free medium or stimulated with 0.1 nM or 1 nM R1881 for 48 hours. 25 µg of cell lysates were loaded in each lane, separated on NUPAGE® (Invitrogen, Carlsbad, Calif.) SDS gel, transferred onto PVDF membranes and Western blotted with 1:10,000 9FY antibody. Identical gels were transferred onto PVDF membranes and probed with 1:1,000 anti-SLC45A3 antibody, 1:3,000 anti-PSA antibody and 1:1000 anti-alpha-tubulin as described above. VCaP, COLO320, MOLT-4 and KG-1 cells were lysed in M-PER® mammalian protein extraction reagent, their protein concentration determined. 25 µg of cell lysates were loaded in each lane, separated on NUPAGE® (Invitrogen, Carlsbad, Calif.) SDS gel, transferred onto PVDF membranes and Western blotted with 1:10,000 9FY antibody as described above.

Consistent with prior results, significant reduction of the endogenous ERG protein levels were detected with the 9FY antibody (1:10,000 dilution) in response to ERG siRNA treatment (FIG. 1B). As an additional control, we also examined the expression response of negatively regulated downstream target genes of ERG, prostein (SLC45A3) and prostate specific antigen, PSA (KLK3) (Sun et al., 2008). As expected, marked upregulation of prostein and PSA was evident in VCaP cells in response to ERG siRNA (FIG. 1A and FIG. 1B, bottom panels).

2. ELISA

In an ELISA assay, we assessed the sensitivity and specificity of the 9FY antibody measuring the titer of various concentrations of the immunizing polypeptide (i.e. amino acids 42-66 of SEQ ID NO: 1). For direct ELISA, plates were first coated with 100 µl of ERG3 antigen at 1 ng/ml, 10 ng/ml, 100 ng/ml and 1 µg/ml and incubated for 16 h at 4° C. on a shaker before washing the plate five times with PBSt (300 µl/well). Biotin-conjugated detecting 9FY antibody diluted in SuperBlock B was added at 74 µg/100 µl/well and the plates were incubated for 1 h on a shaker (this and all subsequent steps are performed at room temperature). The plate was washed with PBSt (300 µl/well). Next StreptAvidin-horse radish peroxidase (HRP) in PBS (100 µl/well) was added and incubated for 30 minutes on a shaker at room temperature. The plate was then washed with PBSt (300 µl/well), before adding TMB at 100 µl/well and allowed to develop for 5 min on a shaker before Stop solution were added at 50 µl/well. Absorbance was measured at 450 nm on a MULTISKAN® Ascent (Thermo Scientific, Waltham, Mass.) ELISA plate reader according to the manufacturer's recommendation and the absorbance were plotted against antibody dilution. For indirect ELISA, plates were first coated with 10011 (570 µg)/well of C-epitope anti-ERG antibody and incubated for 16 h at 4° C. SuperBlock (Cat. #PI-37515, Thermo Scientific, Rockford Ill.) was added at 300 µl/well and incubate for 1 h (this and all subsequent steps are performed at room temperature) on a shaker. 200 ng ERG3 antigen were added at (100 µl/well) and incubated for 2 hours on a shaker before the plate was washed with PBSt (300 µl/well). Biotin-conjugated detecting 9FY antibody diluted in SuperBlock B was added at 74 µg/100 µl/well and the plates were incubated for 1 h on a shaker. The plate was washed with PBSt (300 µl/well) and StreptAvidin-HRP in PBS (100 µl/well) were next added and incubated for 0.5-h on a shaker (room temperature). The plate was washed with PBSt (300 µl/well) again. Then tetramethylbenzidine (TMB) was added at 100 ul/well and allowed to develop for 5 min on a shaker before Stop solution was added at 50 µl/well. Absorbance was measured at 450 nm on a MULTISKAN® Ascent (Thermo Scientific, Waltham, Mass.) ELISA plate reader according to the manufacturer's recommendation and the absorbance was plotted against antibody dilution.

Figure 2A:
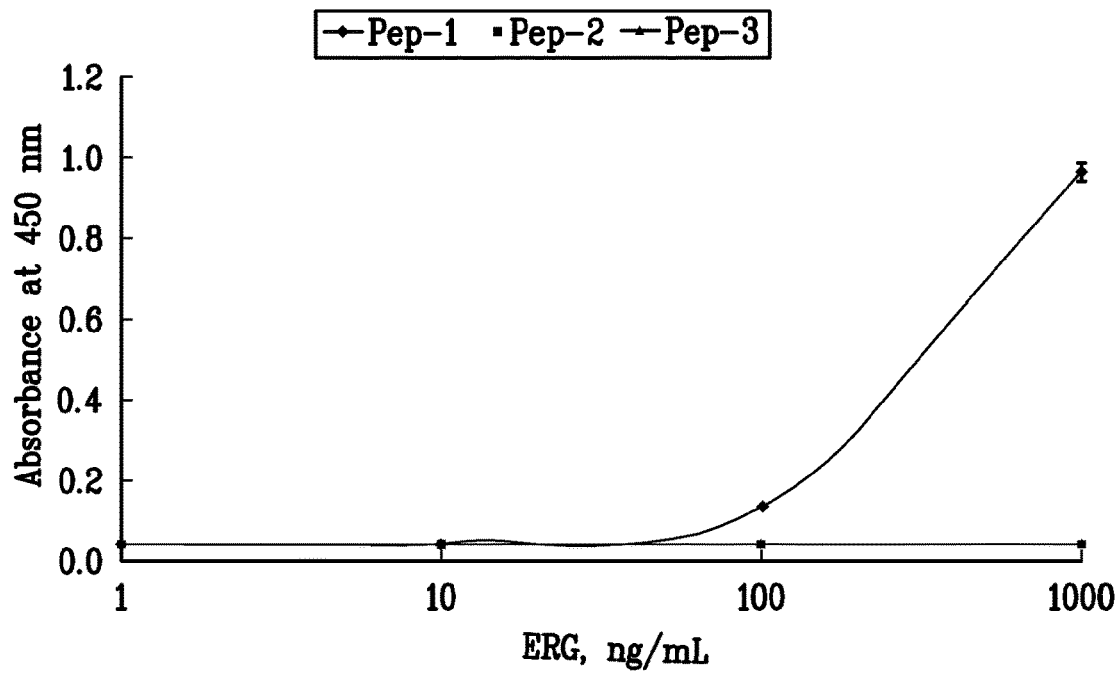
FIG. 2A shows that the 9FY antibody recognizes the immunizing polypeptide in an ELISA assay. Various concentrations of the immunizing polypeptide and two control polypeptides were plated in wells for ELISA and were probed with 1:10,000 dilution of 9FY antibody. Y-axis indicates absorbance values at 450 nm. On the X-axis the log 10 concentration of the ERG immunizing polypeptide and control polypeptides is shown in ng/ml.
Figure 2B:
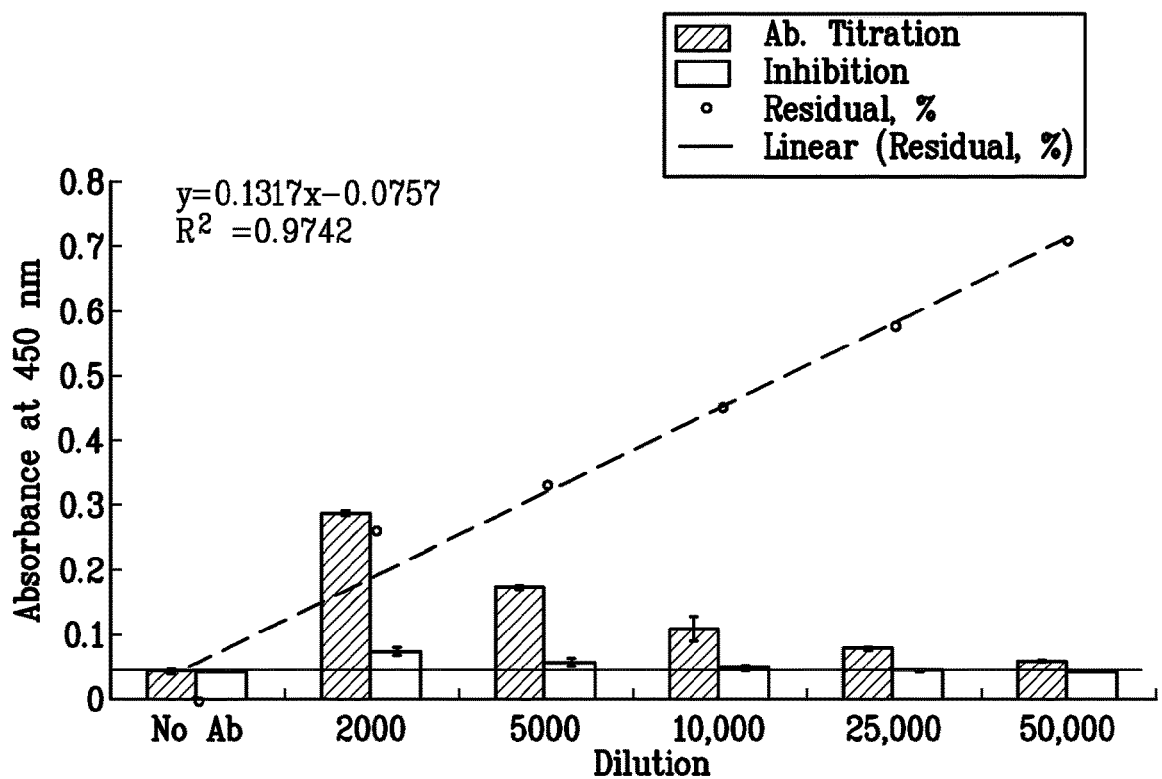
FIG. 2B shows that the immunizing polypeptide competes with ERG3 protein for 9FY antibody binding. In sandwich ELISA assay, ERG3 protein lysates were plated in multi-well format plates and were assayed with various concentrations of 9FY antibody in the presence (white bar) or absence of the immunizing polypeptide (shaded bar). Fold dilution is marked on the X-axis. Antibody titration values are marked by shaded bars.

The 9FY antibody recognized the immunizing polypeptide corresponding to amino acids 42-66 of SEQ ID NO: 1. Antibody titration and competitive inhibition assay revealed that the immunizing polypeptide, but not two control polypeptides, competes for the 9FY antibody binding against the ERG3 protein (FIG. 2A) and that purified 9FY antibody can detect in the 5000-20000× dilution range (FIG. 2B).

3. In Vivo Chromatin Immunoprecipitation Assay

Figure 3:
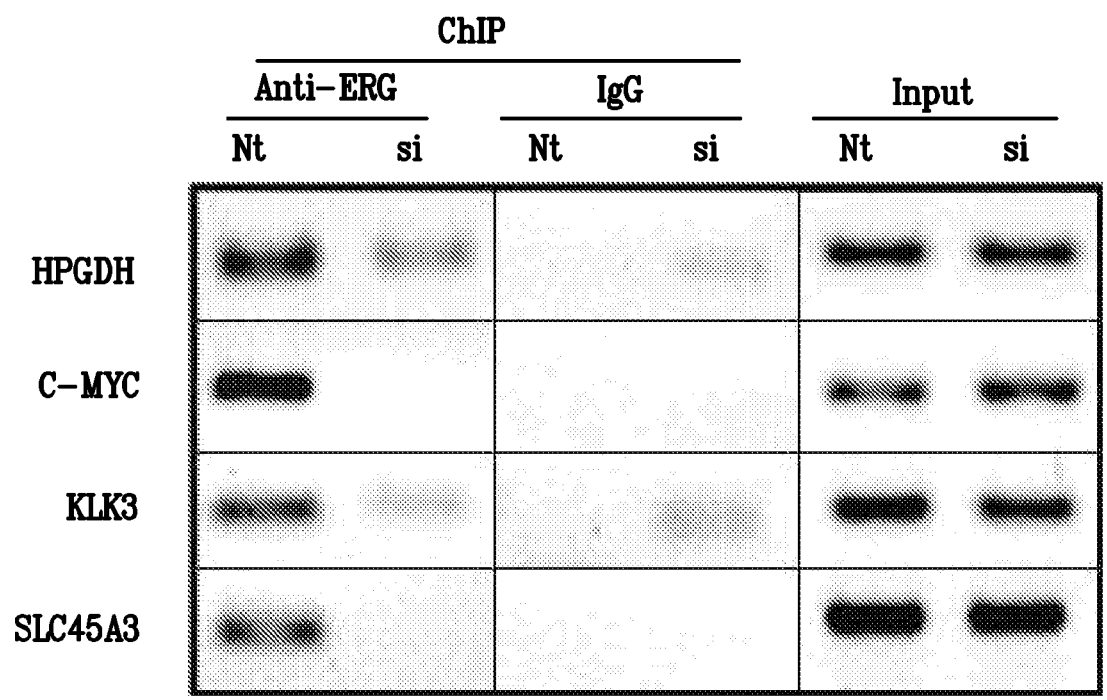
FIG. 3 shows that the 9FY antibody recognizes and immunoprecipitates ERG protein from genomic target sites as shown by in vivo chromatin immunoprecipitation assay (ChIP). R1881 treated VCaP cells were transfected by either ERG siRNA (si) to knock-down ERG or by control Non-targeting (NT) siRNA. Cells were processed for ChIP assay and the chromatin was immunoprecipitated by using 9FY antibody. In control (NT) transfected cells ERG protein is recruited to HPGDH, C-MYC, KLK3 (PSA) and SLC45A3 (prostein) genomic target sequences. ERG knockdown strongly reduces ERG recruitment to the genomic target sites. Input genomic DNA amplicons were used as controls for the ChIP assay.
Figure 5A:
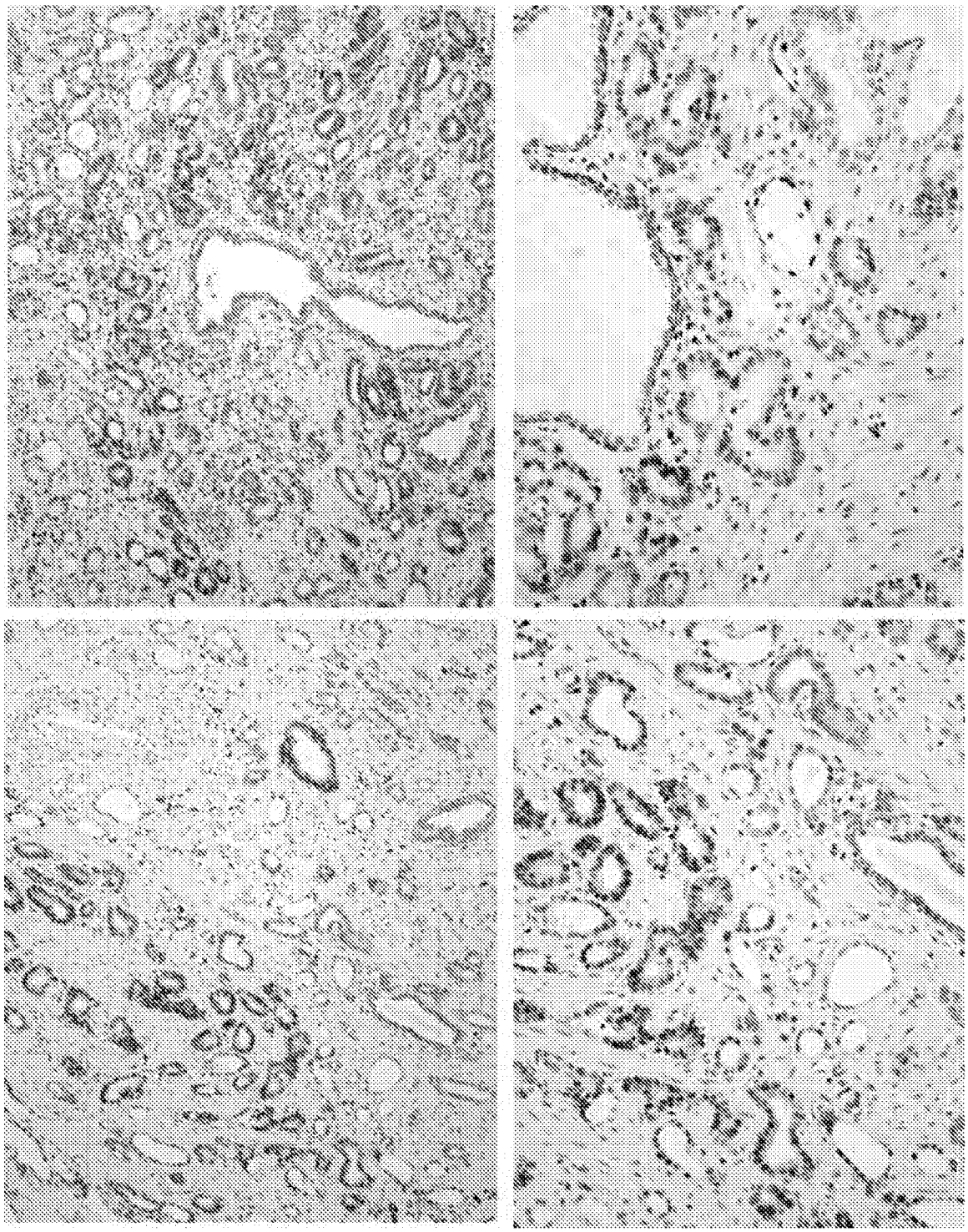
FIGS. 5A-D show that the 9FY antibody specifically stains prostate tumor epithelial cells in formalin fixed paraffin embedded (FFPE) human prostate radical prostatectomy specimens assayed by immunohistochemistry (IHC).
Figure 5B:
Figure 5C:
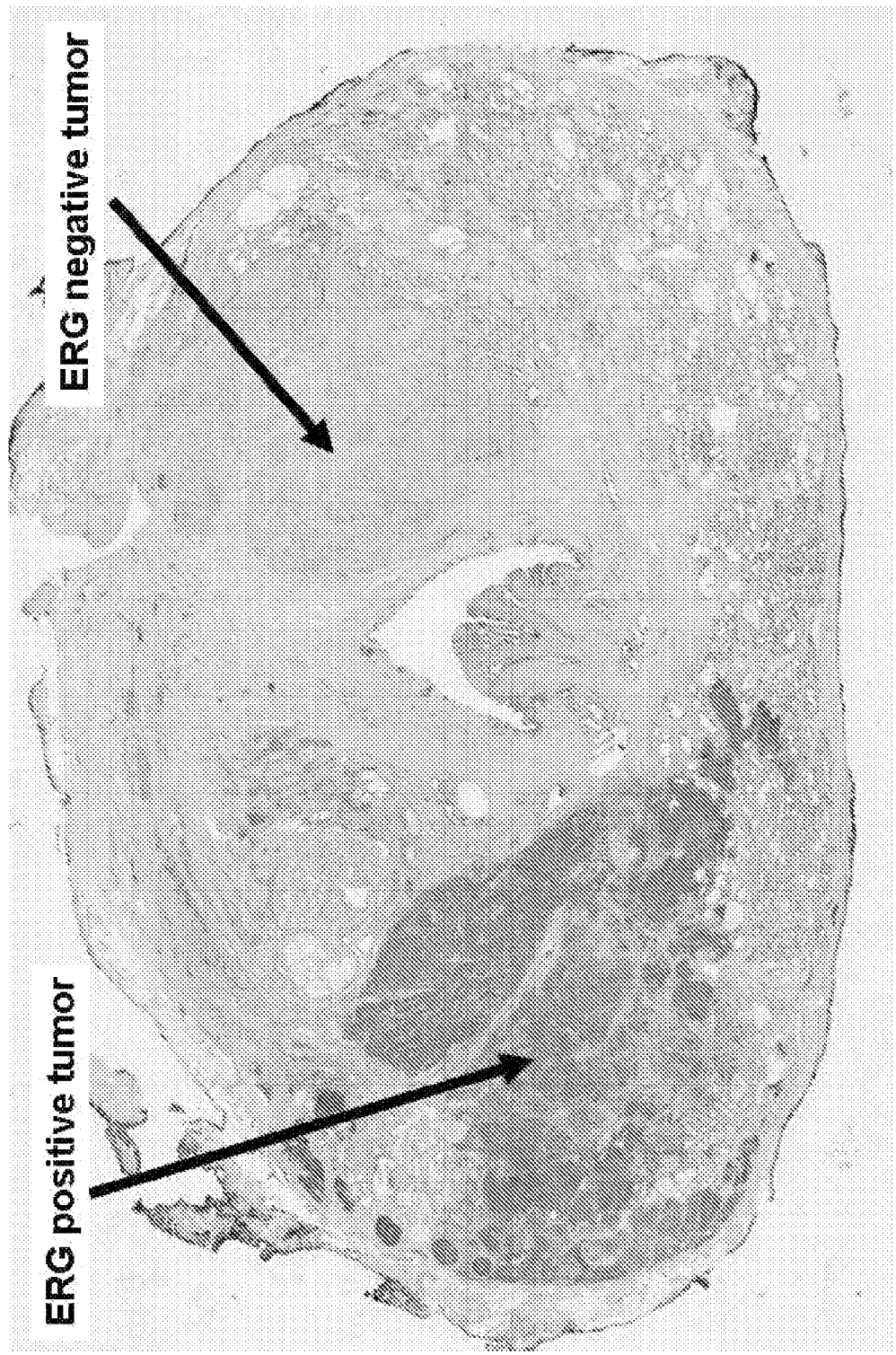
Figure 5D:
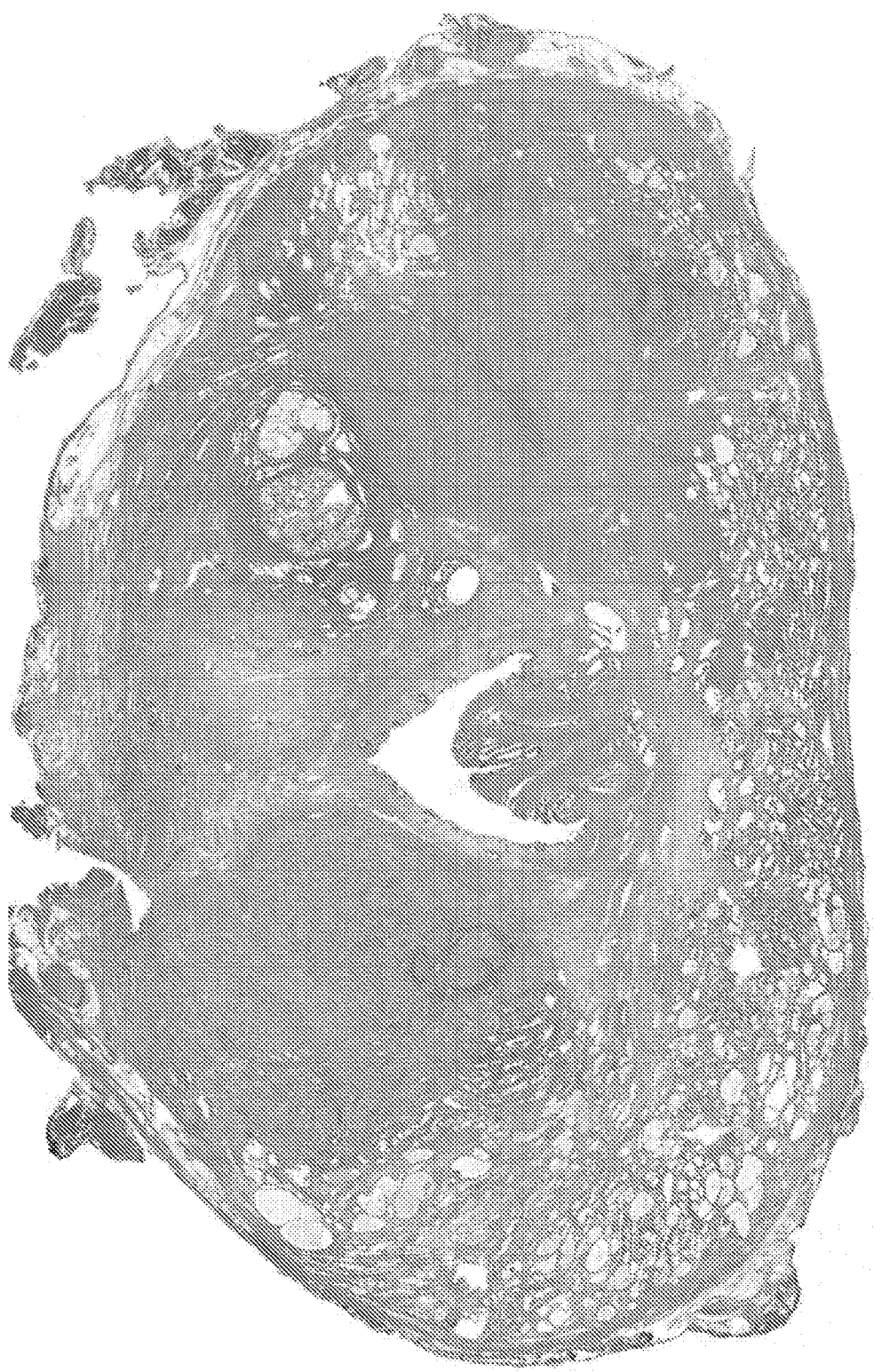

To further assess the specificity of the 9FY antibody, we tested the recruitment of endogenous ERG to previously defined gene regulatory elements by in vivo chromatin immunoprecipitation (ChIP) assay (Sun et al., 2008). Expression of ERG protein encoded by a TMPRSS2/ERG fusion transcript was induced by R1881 in VCaP cells, and the cells were transfected by either ERG siRNA to knockdown ERG or by control Non-targeting (NT) siRNA. The cells were processed for ChIP assay and the chromatin was immunoprecipitated using the 9FY antibody. In the absence of ERG siRNA, endogenous ERG protein is recruited to target gene sequences. In contrast, robust reduction of the ERG protein binding to the HPGDH, C-MYC, prostein (SLC45A3) and PSAlKLK3 gene regulatory regions (FIG. 3) was observed in response to ERG knockdown. This result is consistent with the specific immunoprecipitation of ERG-bound chromatin by the antibody.

4. Immunofluorescence (IF)

The 9FY antibody was further evaluated in VCaP cells by the IF method (FIG. 4). VCaP cells were transfected with either NT- or ERG-siRNA oligonucleotides, the growth media were replaced with fresh DMEM supplemented with 10% charcoal stripped serum and 0.1 nM R1881 and further incubated for 48 hours. For immunostaining, cells were first fixed in fresh 4% Formaldehyde in phosphate buffered saline (PBS) and permeabilized in PBS-T (PBS+0.1% TritonX-100) before being centrifuged onto glass slides with a CYTOSPIN® 4 (Thermo Scientific, Waltham, Mass.) centrifuge. Cells were then blocked in PBS-NT20 (PBS supplemented with 1% normal horse serum (Cat #S-2000, Vector laboratories, Burlingame, Calif.) and 0.1% Tween-20. Cells were then incubated with primary antibody against SLC45A3 or PSA (both from DAKO, Carpinteria, Calif.), diluted in PBS-NT20, at room temperature. Cells were washed with PBS-NT20 before goat anti-mouse ALEXA FLUOR® 594 (Invitrogen, Carlsbad, Calif.; Cat #A11302), goat anti-rabbit ALEXA FLUOR® 488 (Invitrogen, Carlsbad, Calif.; Cat #A11304) secondary antibodies and DAPI were applied. Cells were washed and mounted with FLUO-ROMOUNT G™ (SouthernBiotech, Birmingham, Ala.) Images were captured using a 40×/0.65 N-Plan objective on a Leica DMIRE2 inverted microscope with a Qlmaging Retiga-EX CCD camera (Burnaby, BC, Canada), operated by OpenLab software (Improvision, Lexington, Mass.). Images were converted into color and merged by using Photoshop (Adobe). For peptide competition, the competitive immunizing polypeptide (amino acids 42-66 of SEQ ID NO: 1) and non competitive, control ERG polypeptides were diluted from a stock solution and mixed with the antibody at an excess of 2000-fold in molar concentration over the antibody in the final concentration. The antibody-polypeptide mixes were incubated on ice for 30 min before applying to tissue specimen as described.

The 9FY antibody specifically recognized ERG protein as shown by nuclear staining characteristic of the transcription factor function of ERG. VCaP cells were transfected with siRNA that efficiently knocks down ERG as it was previously shown (Sun et al., 2008). Indeed, robust reduction of endogenous ERG protein levels was observed in response to ERG siRNA treatment compared to cells treated with control no-targeting siRNA. ERG is a repressor of prostate differentiation marker genes (Sun et al., 2008; Tomlins et al., 2008). Thus, elevation of PSA levels is consistent with efficient ERG knockdown (FIG. 4A). To establish the recognition specificity of the 9FY antibody, the antibody was competed with a 2000× excess of the competitive immunizing polypeptide prior to the IF assay on VCaP cells. A 2000× fold molar excess of the immunizing polypeptide (Competing peptide) was sufficient to eliminate the IF signal in a 9FY antibody-specific manner. By contrast, control ERG polypeptides (Non-competing peptide) failed to compete with the 9FY antibody (FIG. 4B). Cytoplasmic Prostate Specific Antigen (PSA) staining is not affected by the immunizing polypeptide or the control polypeptide. Hormone inducible cytoplasmic expression of PSA was used as a positive control for androgenic activation of ERG and PSA gene expressions (FIG. 4C). In LNCaP cells that neither harbor TMPRSS2/ERG fusions nor express detectable levels of endogenous ERG, the 9FY antibody did not recognize ERG. PSA protein expression in response to R1881 is easily detectable in LNCaP cells and is consistent with the androgen-inducible expression of PSA. Towards defining the concentration range for 9FY antibody specificity we found that ERG recognition by the 9FY antibody meets the criteria even in the concentration range from 1:5,000 to 1:20,000 dilution of 3.7 mg/ml stock (FIG. 4D). In the absence of 9FY antibody, the secondary antibody fails to detect any epitopes in VCaP cells. This result excluded the possibility of non-specific staining of background proteins in the IF experiments (FIG. 4E).

Example 3. Immunohistochemical Staining in FFPE Specimens

The 9FY antibody was also tested in formalin-fixed paraffin embedded (FFPE) human prostate specimens. Radical prostatectomy specimens were fixed in formalin and embedded as whole mounts in paraffin. Each prostate was sectioned at 0.22 cm intervals in a transverse plane perpendicular to the long axis of the posterior surface of the prostate and completely embedded as whole mounts. The sections were analyzed for immunohistochemistry (IHC) staining on four-micron sections of the whole-mounted blocks.

The tissue sections for IHC were prepared as described previously (Furusato et al., 2007). Slides were incubated with 1:1200 9FY antibody. VECTOR® VIP (Vector Laboratories, Burlingame, Calif.) (purple) was used as chromogen substrate and the slides were counterstained with hematoxylin. IHC revealed nuclear staining of prostate tumor cells that is consistent with the sub-cellular localization of the ERG transcription factor (FIGS. 5A-5D). In contrast, 9FY antibody stains neither normal epithelia nor stroma in the human prostate. Endothelial cells of vasculature showed staining with 9FY antibody that is consistent with the established constitutive expression of wild-type ERG in endothelial cells (Birdsey et al., 2008; McLaughlin et al., 1999; Rainis et al., 2005). Thus, endothelial cell staining can be used by pathologists as an internal reference when tumor epithelial IHC reactivity is observed with the 9FY antibody. Evaluation of whole mount specimens from 150 plus prostate cancer patients has confirmed the specificity of the 9FY antibody.

Example 4. Detection of ERG Protein in Other Cancer Cell Lines

Figure 6:
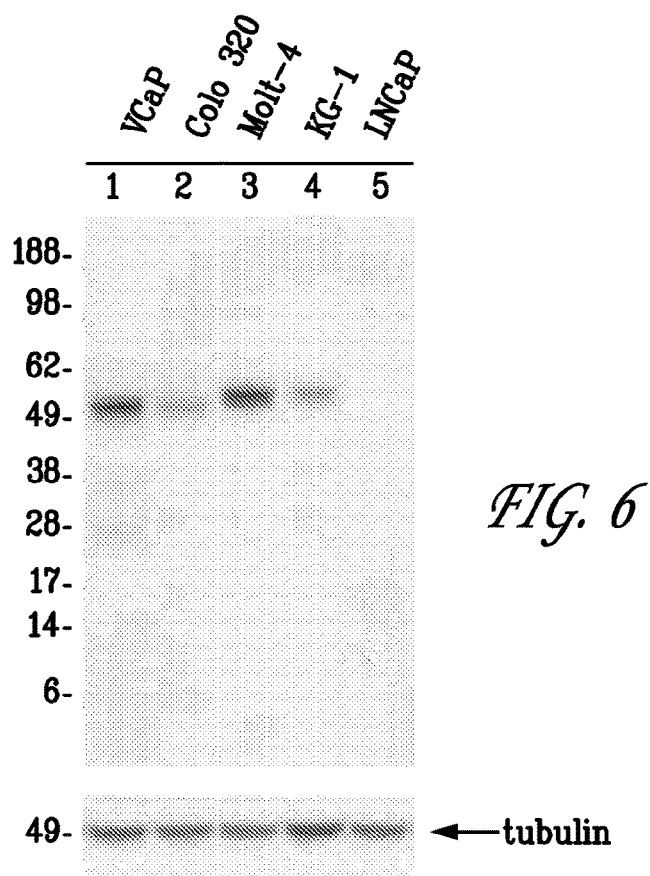
FIG. 6 shows that endogenously expressed ERG protein is detected by 9FY antibody in colon cancer (COLO 320), acute myeloid leukemia (KG1), and human acute T lymphoblast leukemia (MOLT4) derived cell lines by using immunoblot assay.

Having established the specificity of the 9FY antibody in the VCaP prostate cancer cell line, we further evaluated this antibody for the detection of ERG protein in cell lines that were previously described to express high levels of ERG RNAs, including COLO 320 (colon cancer (Quinn et al., 1979)), KG1 (acute myeloid leukemia, (Koeffler and Golde, 1978)) and MOLT4 (human acute T lymphoblast leukemia (Minowada et al., 1972)). Colo320 (ATCC #CCL-220.1) and MOLT-4 (ATCC #CRL-1582) cells were grown in RPMI-1640 supplemented with 10% FBS. KG-1 cells were grown in Iscove modified DMEM (Cat #12440-053, Invitrogen, Carlsbad, Calif.) supplemented with 10% FBS. Cells were harvested and analyzed by Western blots and microscopy as described above. Immunoblot assay of COLO 320 (colon cancer (Quinn et al., 1979)), KG1 (acute myeloid leukemia, (Koeffler and Golde, 1978)) and MOLT4 (human acute T lymphoblast leukemia (Minowada et al., 1972)) with the 9FY antibody detected one predominant protein species (FIG. 6), indicating the usefulness of this antibody in detecting and evaluating ERG proteins in human cancers other than prostate cancer.

Example 5. Specificity of the 9FY Antibody

1. Western Blots

Figure 7:
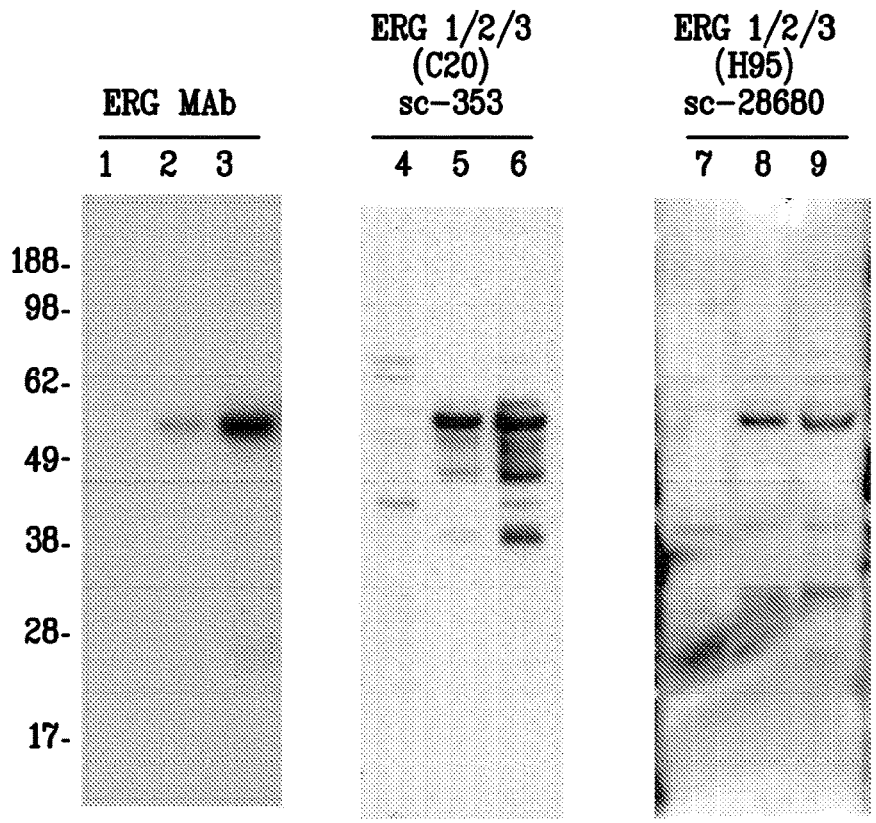
FIG. 7 shows that the 9FY antibody specifically detects exogenously overexpressed ERG protein encoded by a TMPRSS2/ERG fusion transcript in immunoblots, whereas commercially available polyclonal antibodies detect multiple proteins in the same cell lysates. 20 gig of control HEK293 cell lysates transfected with empty vectors were loaded in lanes 1, 4 and 7; 4 µg and 20 gig of lysates from pIRES-TMPRSS2-ERG3 transfected HEK293 cells were loaded in lanes 2, 5 and 8, and lanes 3, 6 and 9, respectively.
Figures 8A, 8B:
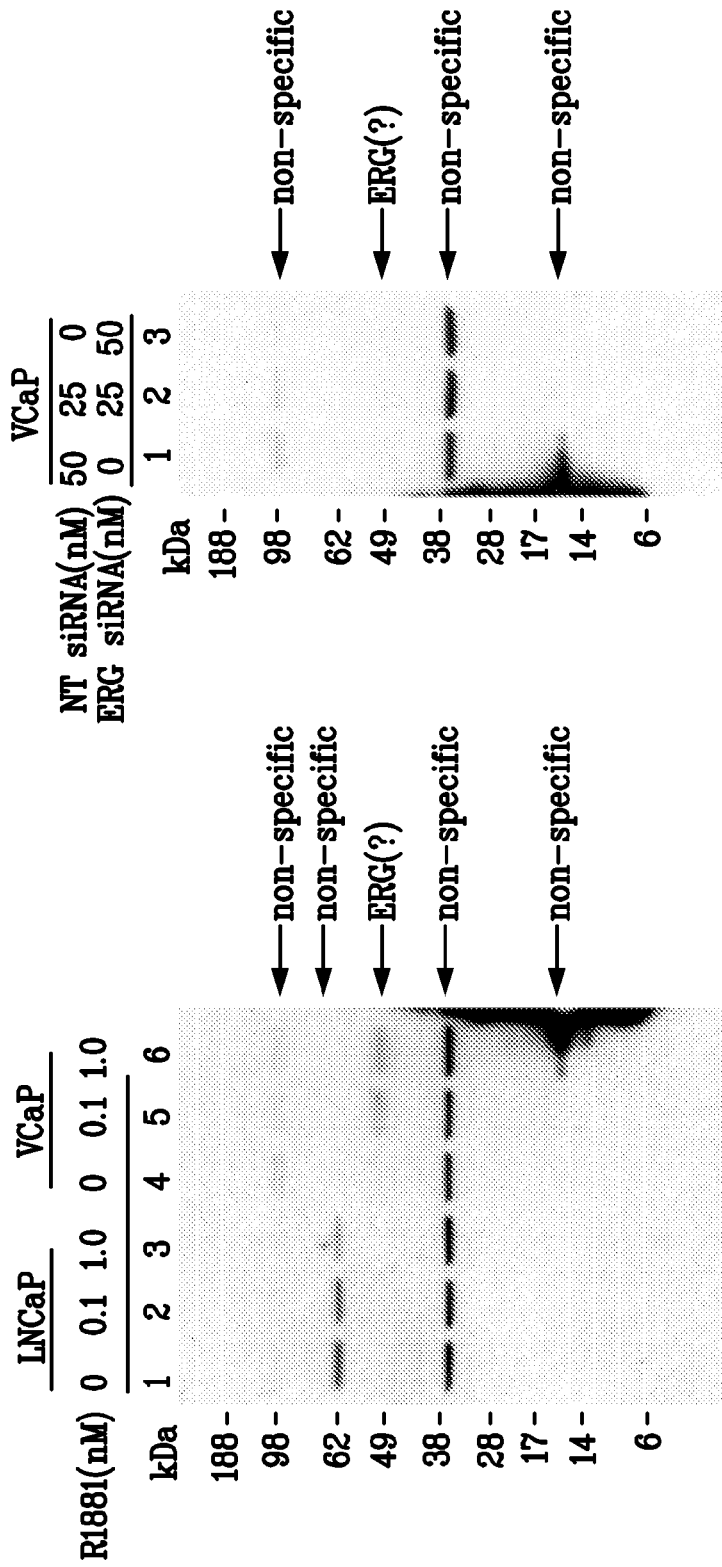
FIG. 8A shows that the polyclonal H95 (sc-28680) antibodies detect multiple non-specific bands in LNCaP and VCaP cell lysates. LNCaP and VCaP cells were treated with (lanes 2, 3, 5, and 6) or without (lanes 1 and 4) the synthetic androgen hormone (R1881).
FIG. 8B shows the non-specific binding of H95 antibodies to unknown proteins in VCaP cells treated with ERG siRNA and/or Non-targeting (NT) RNA. In the absence of ERG siRNA, H95 antibodies do not appear to detect ERG expression. Furthermore, H95 antibodies do not permit one to observe the inhibition of ERG expression by ERG siRNA.

Using Western blots, the specificity of the 9FY antibody was compared to commercially available polyclonal anti-ERG antibodies (C-20 (sc-353) or H95 (sc-28680)) using cell lysates from HEK293 cells transfected with a TMPRSS2/ERG3 fusion transcript. The 9FY antibody was used at 1:5000; C20 (sc-353) (Santa Cruz Biotechnology, Inc, Santa Cruz, Calif.) and H95 (sc-28680) (Santa Cruz Biotechnology, Inc, Santa Cruz, Calif.) were used at 1:1000 dilutions. The 9FY antibody detects the exogenously expressed ERG protein encoded by the TMPRSS2/ERG3 fusion transcript (52 kDa) as a single species in Western blots of TMPRSS2/ERG3 transfected HEK293 cells, highlighting the specificity of the 9FY antibody (FIG. 7). On the other hand, commercially available anti-ERG polyclonal antibodies react with multiple proteins in identical blots. Specifically, the commercially available polyclonal C20 antibodies (sc-353) and polyclonal H95 antibodies (sc-28680) lacked the specificity of the 9FY antibody, as evidenced by the multiple bands in the Western blots obtained with those polyclonal antibodies (FIG. 7). According to the available product literature, C20 recognizes an epitope mapping to the C-terminus of human ERG1, ERG2 and ERG3, while H95 recognizes an epitope mapping to amino acids 26-120 of human ERG2 and ERG3 (Owczarek et al 2004).

The specificity of the polyclonal H95 antibodies was further analyzed using cell lysates from LNCaP and VCaP cells. Lysates were prepared from LNCaP and VCaP cells treated with or without the R1881 androgen or transfected with Non Targeting (NT) or ERG siRNA oligonucleotides, as described above. Notably, the H95 antibodies detected multiple non-specific bands in LNCaP and VCaP cell lysates and questionable detection of the target, a 52 kDa, truncated ERG polypeptide encoded by a TMPRSS2/ERG fusion transcript (compare FIGS. 9A/B with FIGS. 1A/B).

Figure 13:
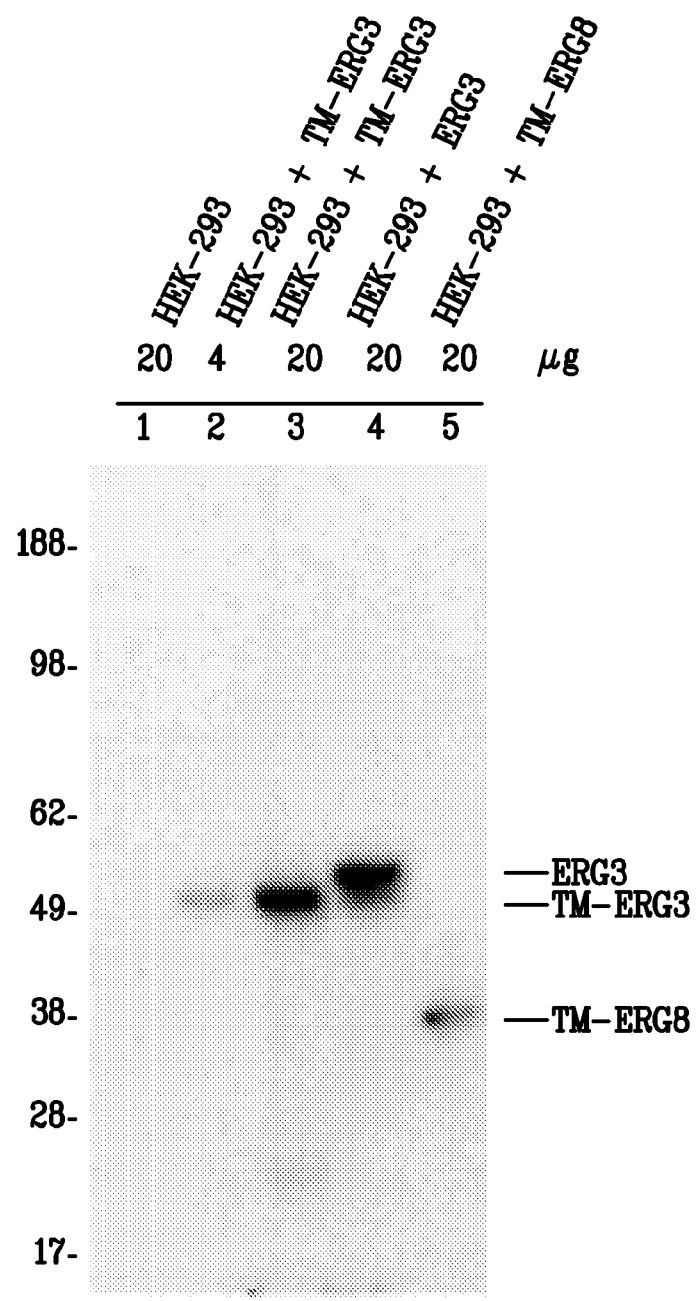
FIG. 13 shows that the 9FY antibody detects ERG oncoprotein products encoded by common splice variants of TMPRSS2-ERG fusions. Specifically, the 9FY antibody recognized ERG oncoprotein products encoded by: TMPRSS2-ERG fusion type-A cDNA (lanes 2 and 3), wild type ERG3 cDNA (lane 4) and TMPRSS2-ERG8 fusion type-A cDNA (lane 5).

The 9FY antibody has also been used to detect an ERG oncoprotein encoded by the TMPRSS2/ERG8 fusion transcript. HEK-293 cells were grown in DMEM medium, supplemented with 10% fetal bovine serum and 2 mM glutamine. HEK-293 cells ($2\times10^6$) were seeded onto 10 cm dishes and maintained for two days, before transfection with 4 μg of plasmid DNA pIRES-EGFP(CMV), pIRES-EGFP(CMV)-TMPRSS2-ERG3, pIRES-EGFP(CMV)-ERG3 or pIRES-EGFP(CMV)-TMPRSS2-ERG8. LIPOFECTAMINE™ 2000 (Invitrogen, Carlsbad, Calif.; Cat #11668-027) was used for transfection, and 48 hours later cells were harvested and total cell lysates equivalent to 4 or 20 gig of protein were analyzed by Western blotting using the 9FY antibody at 1:5000 dilution. The 9FY antibody recognized predominant protein bands consistent with the predicted sizes of the wild type ERG3 protein (53 kDa), the TMPRSS2/ERG3 encoded oncoprotein (50-52 kDa), and the TMPRSS2/ERG8 encoded protein (37 kDa) (FIG. 13).

The immunizing polypeptide showed no significant homology with proteins belonging to the human ETS family of proteins, except for a segment of the human FLi1 protein (Kubo et al., 2003) having 48% sequence identity with the immunizing peptide. Therefore, the 9FY antibody was tested to see if it can discriminate between human ERG3 and the human FLi1 protein using Western blot assays. In this assay, transiently expressed human ERG3 (encoded by TMPRSS2/ERG3 construct) or human FLi1 protein was evaluated with the 9FY antibody. To assure that comparable amount of the human FLi1 protein was present in the assay both ERG3 and human FLi1 proteins were expressed with C-terminal and with N-terminal FLAG tags, respectively. The 9FY antibody recognized only ERG3 protein and showed no immunoreactivity with the human FLi1 protein.

2. Immunofluoresence (IF) Staining

Figure 9A:
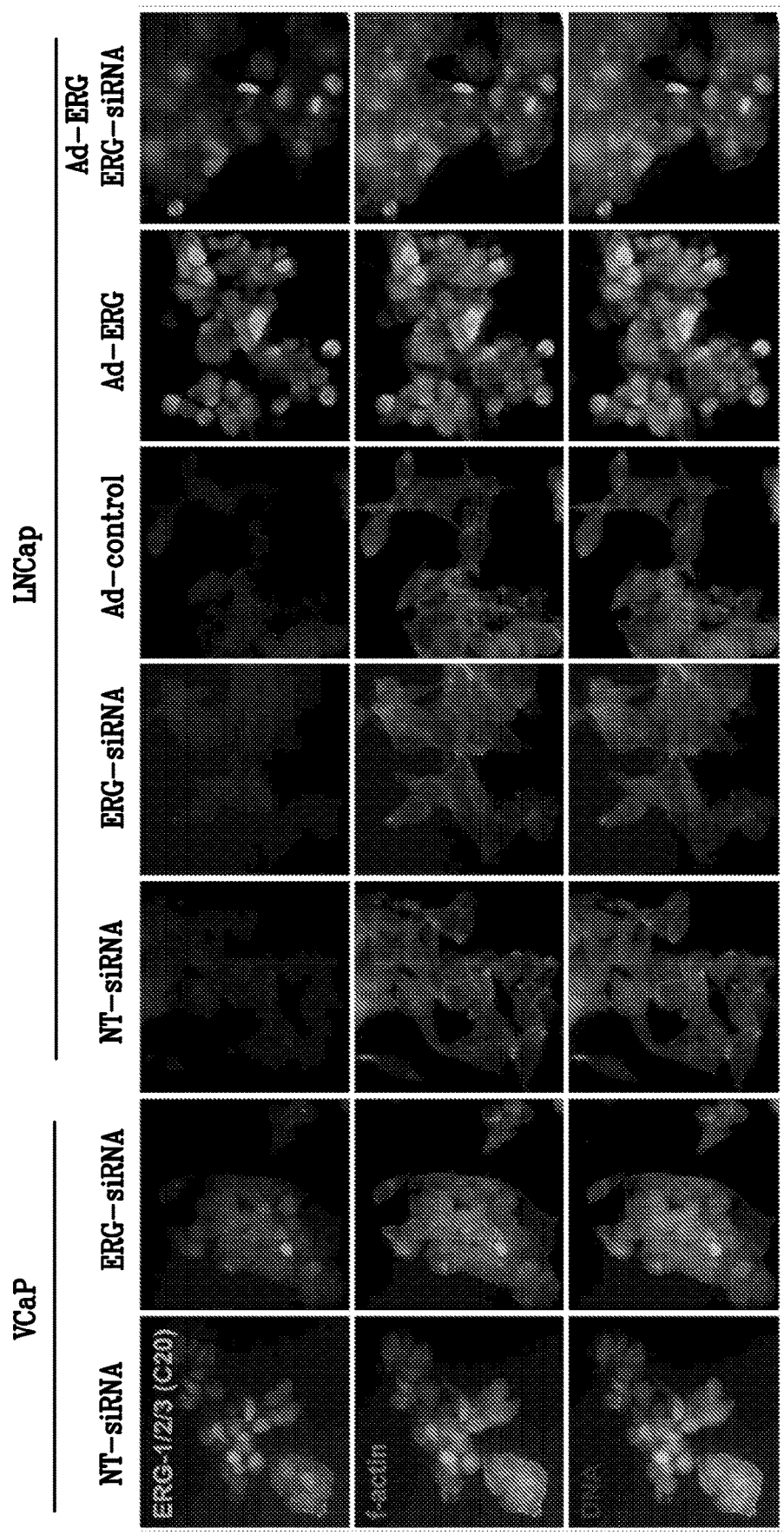
FIGS. 9A and B shows that the commercially available C-20 polyclonal antibodies (sc-353) recognize not only nuclear ERG protein but also non-specific cytoplasmic proteins in an IF assay.

The specificity of the C20 and H95 antibodies were further analyzed using IF assays. Whereas the 9FY antibody exhibited nuclear staining of prostate tumor cells (FIG. 4) in IF assays, polyclonal C20 (sc-353) antibodies recognize not only nuclear ERG protein but also non-specific cytoplasmic proteins (FIG. 9A, column 1) in VCaP cells. ERG knockdown with ERG siRNA did not completely eliminate nuclear ERG and non-specific cytoplasmic staining (FIG. 9A, column 2) of the C-20 antibodies. The C20 (sc-353) antibodies recognize ERG3 overexpressed in LNCaP cells by infection with Ad-ERG3Adenoviral constructs (FIG. 9A, column 6) but the staining was still detected after knockdown with ERG siRNA (FIG. 9A, column 7). Negative control experiments for siRNA and adenoviral infection are shown in FIG. 9A, columns 3, 4 and 5.

Figure 9B:
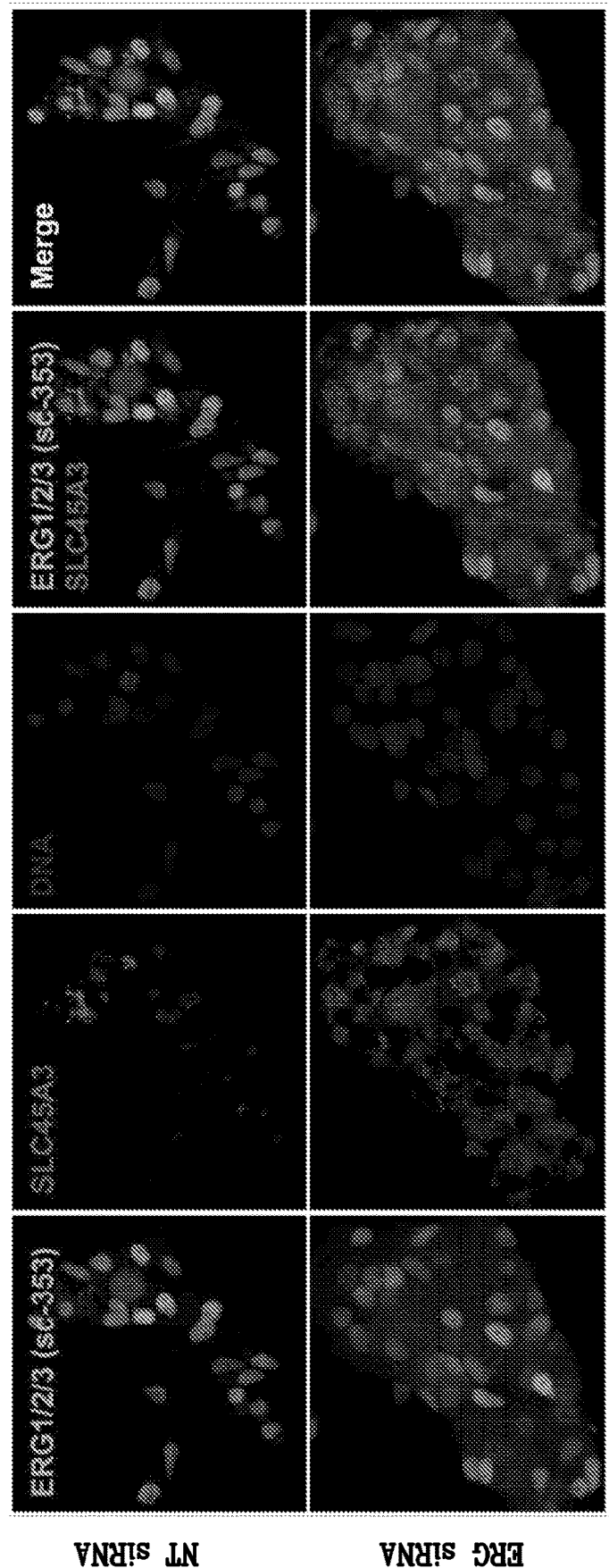

The C20 (sc-353) antibodies recognize nuclear ERG protein in VCaP cells (FIG. 9B, column 1, upper panel). However, knockdown with ERG siRNA did not eliminate nuclear ERG staining but rather resulted in increased background (FIG. 9B, column 1, lower panel). In FIGS. 9A and 9B, ERG is stained by primary C20 (sc-353) antibodies followed by goat anti-rabbit ALEXA FLUOR® 488 (Invitrogen, Carlsbad, Calif.) secondary antibody (green). In FIG. 9A, cells were counter stained with ALEXA FLUOR® 594 tagged phalloidin (Invitrogen, Carlsbad, Calif.; Cat #A12381) to outline the nuclear structure. In FIG. 9B, the androgen inducible SLC45A3 that is negatively controlled by ERG is stained by mouse monoclonal anti-SLC45A3 followed by goat anti-mouse ALEXA FLUOR® 594 (Invitrogen, Carlsbad, Calif.) secondary antibody (red). DNA is stained by DAPI (blue).

Figure 10:
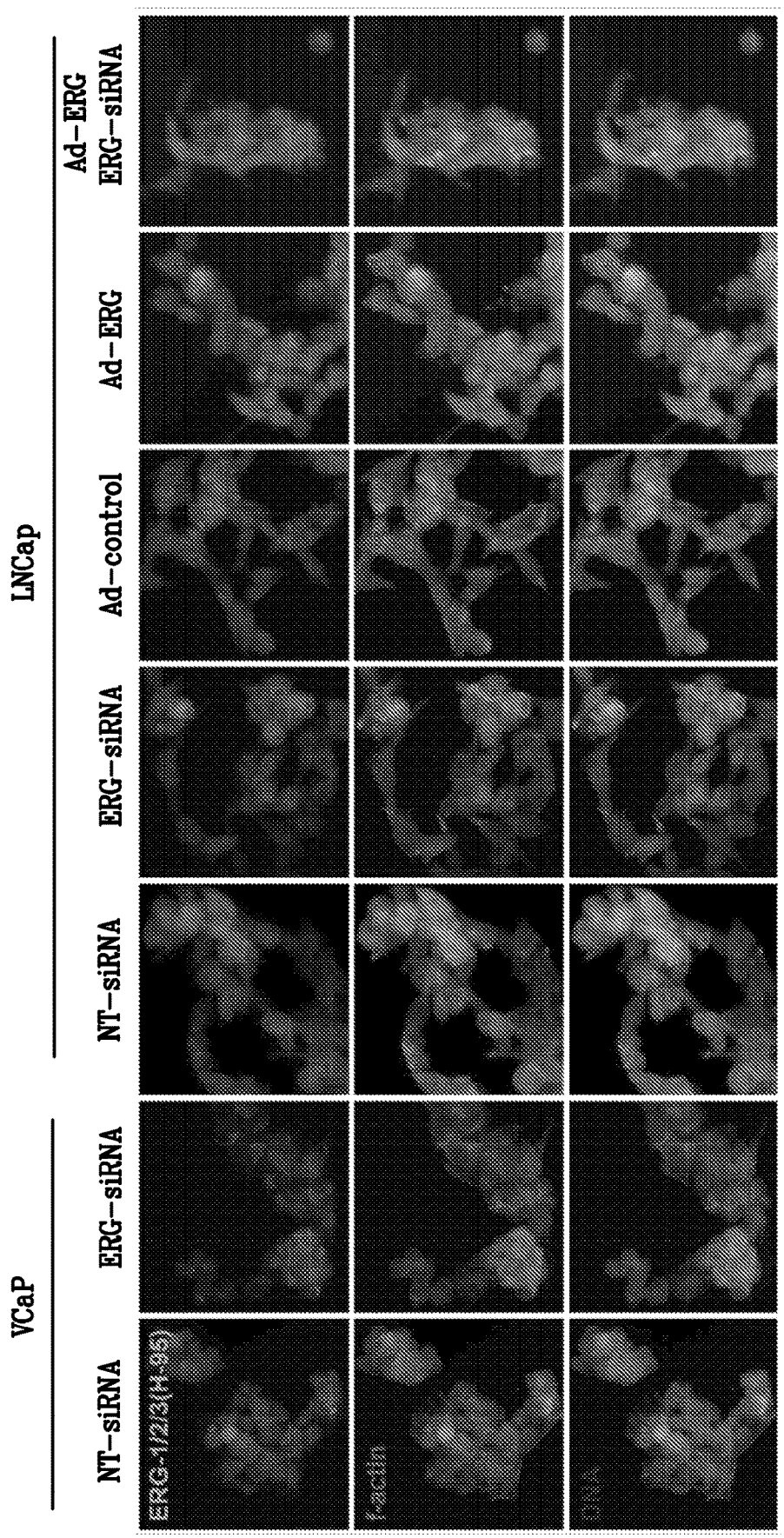
FIG. 10 shows that the commercially available H95 polyclonal antibodies (sc-28680) exhibit non-specific nuclear and cytoplasmic staining in both VCaP and LNCaP cells in an IF assay.

The H95 (sc-28680) antibodies, like the C-20 antibodies, stained nuclear proteins and non-specific cytoplasmic proteins (FIG. 10, column 1) in VCaP cells. In addition, ERG knockdown with ERG siRNA did not show any significant difference in staining (FIG. 10, column 2) in VCaP cells. ERG3 overexpressed in LNCaP cells by infection with Ad-ERG3 adenoviral constructs was detected by H95 (sc-28680) (FIG. 10, column 6) but the staining was not affected by knockdown with ERG siRNA (FIG. 10, column 7). Moreover, in a negative control experiment for siRNA and adenoviral infection (FIG. 10, columns 3, 4 and 5) in LNCaP cells (that do not harbor TMPRSS2/ERG fusion or express detectable levels of endogenous ERG), the H95 (sc-28680) antibodies show high levels of non-specific background staining. In FIG. 10, ERG is stained by primary H95 (sc-28680) followed by goat anti-rabbit ALEXA FLUOR® 488 (Invitrogen, Carlsbad, Calif.) secondary antibody (green). Cells were counter stained with ALEXA FLUOR® 594 (Invitrogen, Carlsbad, Calif.) tagged phalloidin to outline the nuclear structure. DNA is stained by DAPI (blue).

Figure 11:
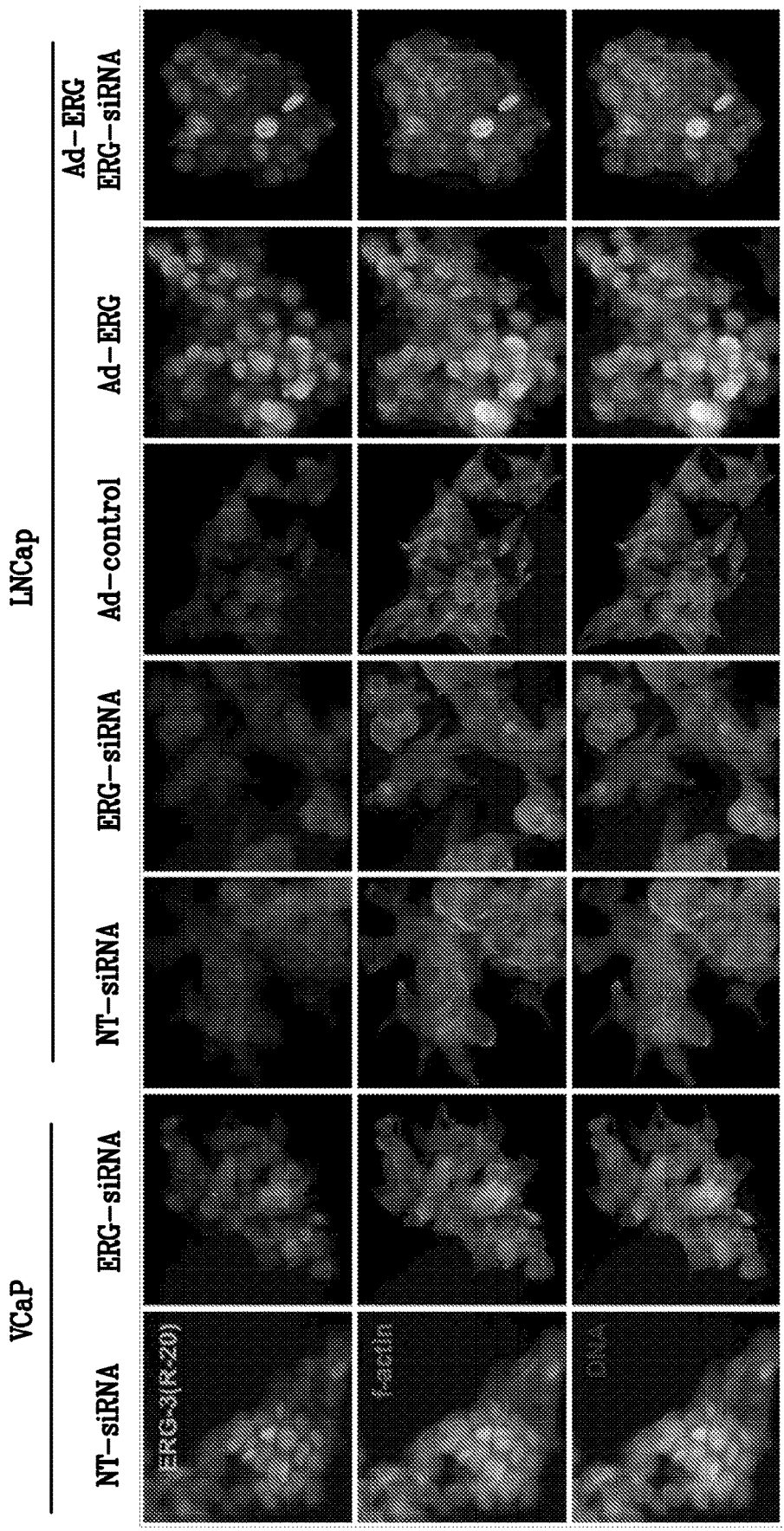
FIG. 11 shows that the commercially available R20 polyclonal antibodies (sc-18136) exhibit non-specific nuclear and cytoplasmic staining in both VCaP and LNCaP cells in an IF assay.

A third commercially available ERG polyclonal antibody, R-20 (sc-18136) (Santa Cruz Biotechnology, Inc, Santa Cruz, Calif.), was also analyzed by IF. According to the product literature available for R-20, it is recommended for detecting ERG3 and binds an epitope that maps to an internal region of human ERG3. ERG-3 R20 (sc-18136) exhibits nuclear staining, as well as non-specific cytoplasmic staining (FIG. 11, column 1). ERG knockdown with ERG siRNA reduced nuclear staining but did not come close to eliminating the nuclear staining (FIG. 11, column 2), as was observed with the 9FY antibody (FIG. 4A). ERG3 over-expressed in LNCaP cells by infection with Ad-ERG3 adenoviral constructs was detected by R20 (sc-18136) (FIG. 11, column 6) but was still detected after knockdown with ERG siRNA (FIG. 11, column 7). The R20 (sc-18136) antibodies also show high levels of background staining in negative control experiment for siRNA and adenoviral infection (FIG. 11, columns 3, 4 and 5). In FIG. 11, ERG is stained by primary R20 (sc-18136) antibodies followed by donkey anti-goat ALEXA FLUOR® 488 (Invitrogen, Carlsbad, Calif.) secondary antibody (green). Cells were counter stained with ALEXA FLUOR® 594 (Invitrogen, Carlsbad, Calif.) tagged phalloidin to outline the nuclear structure. DNA was stained by DAPI (blue).

Figure 12:
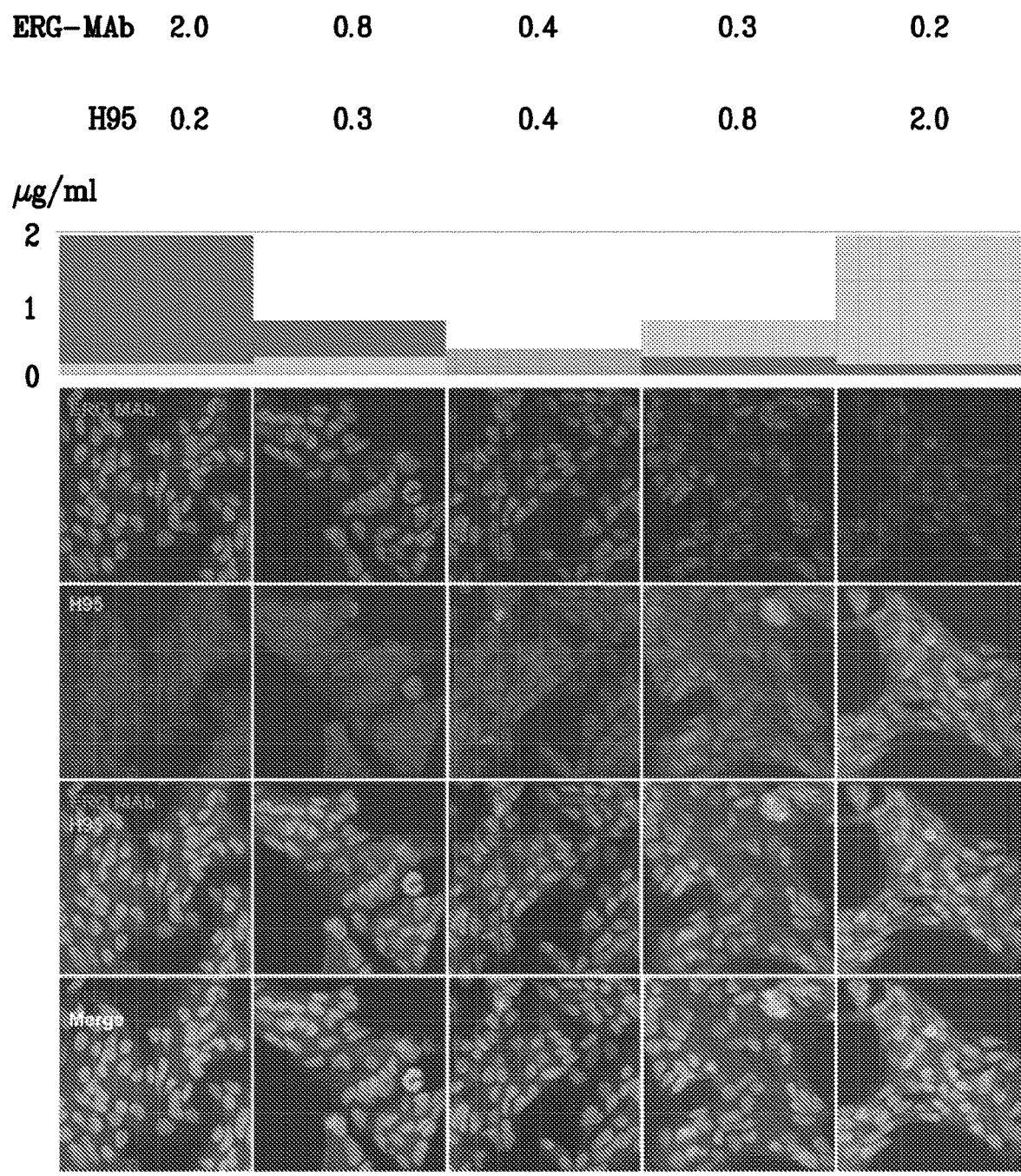
FIG. 12 shows the results of a competitive IF assay in VCaP cells between the 9FY antibody (ERG-MAb) and the commercially available H95 polyclonal antibodies (sc-28680).

Another IF assay was conducted to assess the ability of H95 and 9FY to competitively inhibit the binding of the other antibody to ERG. The results of this competitive IF assay confirm that the 9FY antibody exclusively stains the nucleus of VCaP cells with high affinity. In contrast, H-95 stains unknown protein(s) in the cytoplasm and nucleus of VCaP cells. In head-to-head cross-competition, 10× excess of the 9FY antibody (2 µg/ml) inhibits the nuclear staining of H-95, however, non-specific cytoplasmic staining by H95 remains (FIG. 12, column 1). In contrast, the 9FY antibody at (0.2 µg/ml) still shows distinct nuclear staining in the presence of 10-fold excess of H-95 (2 µg/ml) (FIG. 12, column 5). At equal concentration of antibodies (0.4 µg/ml) the 9FY antibody shows stronger, highly specific and distinct nuclear staining as compared to H95 (FIG. 12, column 3).

Consistent with the other antibody studies discussed above, these results show that the 9FY antibody recognizes a single protein in the nucleus of VCaP cells. In contrast, the H-95 polyclonal antibodies react with multiple undefined proteins in both the cytoplasm and nucleus. Furthermore, the 9FY antibody shows higher affinity when compared to H95.

3. Immunohistochemistry Staining

Using immunohistochemistry staining, the specificity of the 9FY antibody was compared to a commercially available polyclonal anti-ERG antibody called C20 (sc 353) (Santa Cruz Biotechnology, Inc, Santa Cruz, Calif.). Because the 9FY antibody specifically recognizes human as well as mouse ERG proteins, ERG specificity was assessed in formalin fixed paraffin embedded (FFPE) tissues from developing and adult mice.

Collection of Mouse Embryos and Adult Tissues.

Mouse embryos at 9.5, 14.5 and 17.5 days after mating were collected from pregnant mice and fixed in 4% paraformaldehyde for 12-24 hours. Tissues from adult male mouse were collected and fixed in 4% paraformaldehyde for 24 hours. The tissues were processed for paraffin embedding and using microtome 4 µm sections were cut on to superfrost double plus slides Immunohistochemistry (IHC) for ERG.

Following deparaffinization, 4 µm sections were dehydrated and blocked in 0.6% hydrogen peroxide in methanol for 20 min. Sections were processed for antigen retrieval in 0.1M citrate buffer for 30 min in a microwave followed by 30 min of cooling. The IHC procedure was carried-out using Mouse-To-Mouse IHC Detection System Kit (Millipore Inc), according to the manufacturer's instruction. Briefly, sections were blocked with Pre-antibody Blocking solution for 10 minutes. The blocking solution was removed, and the sections were incubated with either the 9FY antibody or the commercially available C20 (sc 353) ERG antibody at a dilution of 1:1000 overnight at 4° C. After the incubation, the slides were washed with PBS for 5 minutes. Slides were incubated with Post-antibody Blocking solution for 10 minutes and washed twice with PBS for 5 minutes each. Slides were incubated with the ready-to-use Poly-HRP-Anti-Mouse/Rabbit IgG for 10 minutes, washed with PBS for 5 minutes, two times and the color was developed with DAB reagent. Sections were then counterstained in hematoxylin for 1 min, dehydrated, cleared, mounted and photographed.

Figure 14:
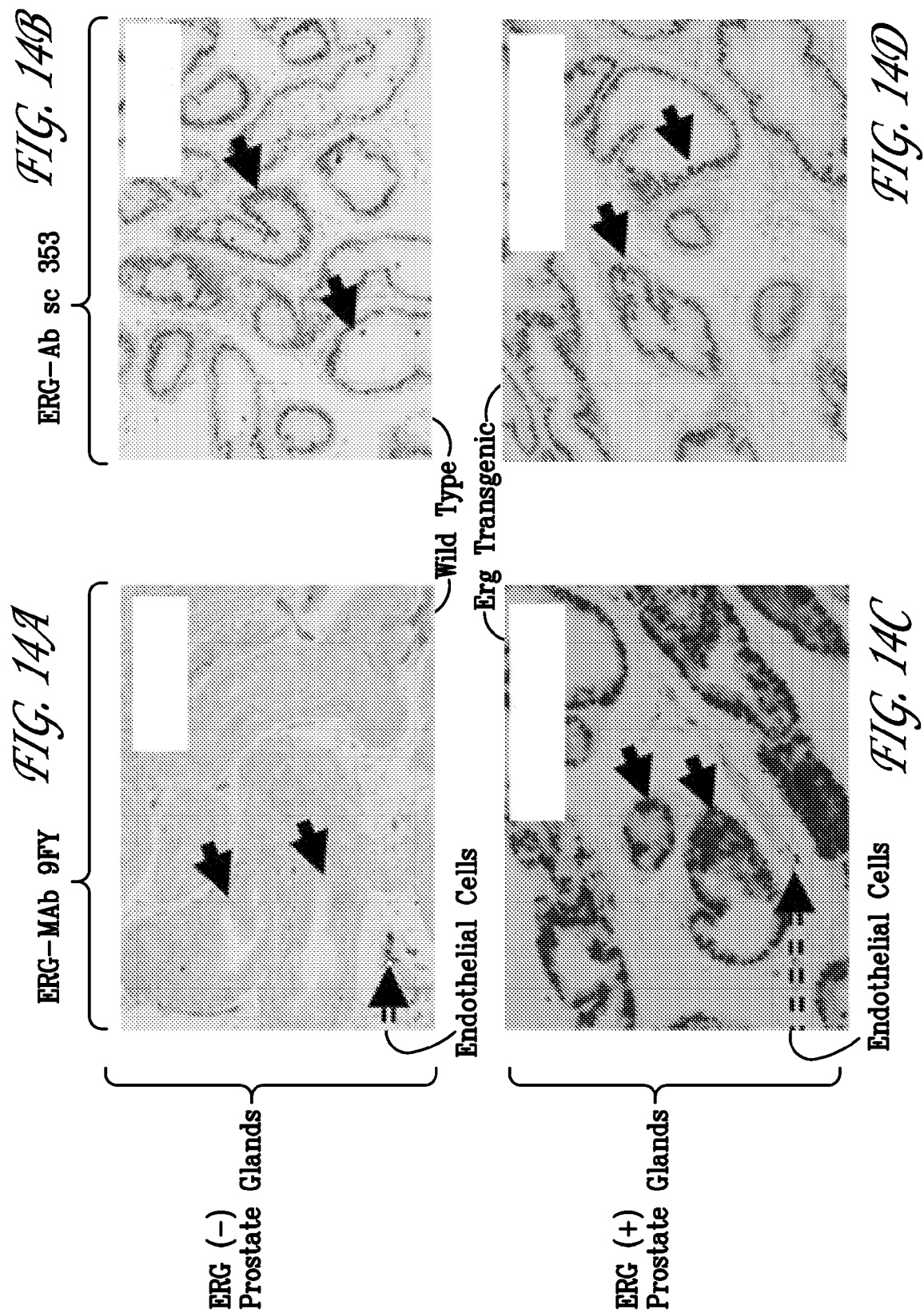
FIGS. 14A-D show the results of a comparative immunohistochemistry analysis between the 9FY antibody and the commercially available C20 (sc 353) antibody (Santa Cruz Biotechnology, Inc, Santa Cruz, Calif.) in prostate tissues obtained from wild type and ERG transgenic mice.

Using the 9FY antibody, ERG was detected only in wild type mouse prostate endothelial cells and was not detected in wild type mouse prostate epithelium. FIG. 14A (Solid arrows mark prostate glands and dashed arrows indicate endothelial cells). On the other hand, the commercially available C20 (sc 353) ERG antibody was non-specific for ERG, staining both prostate endothelial and epithelial cells in tissues obtained from wild type mice. FIG. 14B. As expected, in transgenic mice expressing ERG, both antibodies detected ERG in prostate endothelial and epithelial cells. FIGS. 14C-D. However, the commercial C20 (sc 353) ERG antibody stains wild type and ERG-positive transgenic tissues with the same intensity. FIGS. 14B and D.

The IHC analysis also revealed ERG expression in hematopoietic cells, endothelial cells, and in blood vessels and capillaries of various embryonic tissues (data not shown). Similarly, expression of ERG in adult mouse tissues was detected in hematopoietic cells, endothelial cells in blood vessels and capillaries (data not shown). It is already known that subsets of AML and Ewing Sarcoma exhibit elevated ERG expression. With the availability of an ERG-specific antibody, ERG alterations in pathologic conditions of hematopoietic cells, endothelial cells in blood vessels and capillaries in various embryonic tissues can be pursued effectively. Interestingly, ERG is not detectable in normal epithelial cells in tissues, including prostate glands. Therefore, the detection of ERG in any tissue other than hematopoietic cells, or endothelial cells in blood vessels and capillaries is an indication of an abnormality and/or pathologic condition, such as, cancer.

Example 6. Sequencing of the 9FY Antibody Variable Domains

RNA was extracted from the 9FY hybridoma cell line and reverse transcribed into cDNA using an oligo d(T) primer specific for messenger RNA. The cDNA product was used as a template for PCR using primers specific to murine antibody heavy and light chain sequences.

The PCR products were cloned into a standard sequencing vector and positive colonies identified by PCR. These colonies were cultured and plasmids miniprepped for sequencing. Sequencing was performed using the dye termination method and analyzed on an ABI3130 genetic analyzer. A consensus sequence for the heavy and light chain variable domains was determined by alignment with the program AlignX.

Based on this alignment, the light chain variable domain of the 9FY antibody was determined to comprise the following amino acid sequence (CDR1 (L1), CDR2 (L2), and CDR3 (L3) are underlined):

(SEQ ID NO: 2)
ENVLTQSPAIMSASLGEKVTLSCRAS<u>SSVYY</u>MFWYQQKSDASPKLWI<u>YT</u>

<u>SNLAPGV</u>PARFSGSGSGNSYSLTISSVEGEDAATYY<u>CLQFSTSPWT</u>FGGG

TKLEIKR

And the heavy chain variable domain of the 9FY antibody was determined to comprise the following amino acid sequence (CDR1 (H1), CDR2 (H2), and CDR3 (H3) are underlined):

(SEQ ID NO: 3)
QIQLVQSGPDLKKPGETVKISCKAS<u>GYTFTNYG</u>INWVKQAPGKGFKWMGW

<u>IDTYTGEP</u>TYVDDFKGRFVFSLETSASTAYLQINNLKNEDTATYFC<u>VRKR</u>

<u>AYDYEIY</u>WGQGTPLTVSS

Example 7. Analysis of ERG Oncoprotein and TMPRSS2/ERG Fusion Status in Prostate Cancer To assess the relationship between ERG oncoprotein staining in tumor specimens and TMPRSS2-ERG fusion status, a comparative analysis was performed on consecutive tissue sections of the ERG oncoprotein positive or ERG oncoprotein negative FFPE specimens for the detection of TMPRSS2-ERG mRNA and overall ERG mRNA.

Prostate Specimens.

Prostate specimens for this analysis and for mapping ERG expression in multi-focal prostate cancer (Example 8) were obtained and prepared as follows. Radical prostatectomy specimens of 132 patients enrolled in the Center for Prostate Disease Research program were obtained by pathologists within 30 minutes after the specimen was surgically removed. Radical prostatectomy specimens were fixed in formalin, embedded as whole mounts in paraffin, sectioned at 0.22 cm intervals in a transverse plane perpendicular to the long axis of the posterior surface of the prostate, and completely embedded as whole mounts, according to our Armed Forces Institute of Pathology (AFIP) protocol (B. Furusato et al., 2008). From each patient, one whole mount cross section containing one to four tumors (mostly two foci) was selected and tumors represented different grades and stages. Each tumor was separately diagnosed in the prostatectomy specimens and slices with more than one tumor focus represented separate tumors.

Immunohistochemistry for ERG.

Following deparaffinization, 4 µm sections were dehydrated and blocked in 0.6% hydrogen peroxide in methanol for 20 min. Sections were processed for antigen retrieval in EDTA (pH, 9.0) for 30 min in a microwave followed by 30 min of cooling in EDTA buffer. Sections were then blocked in 1% horse serum for 40 minutes followed by incubation with the 9FY monoclonal antibody at a dilution of 1:1280 for 60 min at room temperature. Sections were incubated with the biotinylated horse anti-mouse antibody at a dilution of 1:200 (Vector Laboratories, Burlingame, Calif.) for 30 min followed by treatment with the ABC Kit (Vector Laboratories, Burlingame, Calif.) for 30 min. The color detection was achieved by treatment with VIP (Vector Laboratories, Burlingame, Calif.) for 5 min. Sections were then counterstained in hematoxylin for 1 min, dehydrated, cleared and mounted. The 9FY staining was determined according to percent of cells positive: up to 25% (1+), >25-50% (2+), >50-75% (3+) and, >75% (4+). The intensity was scored as mild (1+), moderate (2+) and marked (3+). A combination of both measurements was calculated by multiplying the percent of positive cells with the degree of intensity, which resulted in a score.

Analysis of ERG mRNA by Branched-Chain DNA (bDNA) Signal Amplification.

One 4 μm-thick section was selected from each of the 35 FFPE whole mount prostate samples. Areas identified as tumors were marked, removed by scraping and homogenized in 600 μl Tissue Homogenization Solution (THS) followed by the addition of 12 μl (50 μg/ml) proteinase K. Specimens were incubated for 7 hrs at 65° C. The samples were centrifuged for 5 minutes at room temperature to pellet any debris. Supernatants were transferred to fresh microfuge tubes, avoiding any residual paraffin. All supernatants were analyzed immediately using the QUANTIGENE® 2.0 Assay (Panomics, Fermont, Calif.). Each sample was assayed in duplicate. Forty μl (5 ng) of the homogenate were used for the amplification of ERG: 80 μl (10 ng) for TMPRSS2-ERG and 5 μl (0.625 ng) for housekeeping genes: ACTB, B2M and RPL19. In addition, VCaP mRNA was used for positive controls. To capture target RNAs, sample dilutions were prepared by combining appropriate volumes of samples in THS. A working probe set for each target was prepared by combining 12 μl of the probe set with 40 μl of the blocking reagent (for target genes only) or 40 μl of nuclease-free water (for 28S RNA), lysis mixture and nuclease-free. The working probe set was mixed and kept at room temperature. To prepare the capture plate, 60 μl of each working probe set was transferred to assigned wells. Assay control and RNA samples were then made up to 100 μl with Hybridization Working Reagent (HWR) and hybridized overnight at 55° C. The plates were washed three times with wash buffer. Preamplifier was then added followed by amplifier, labeled probe and finally the chemi-luminescence substrate with washes after incubation in each reagent. The read-outs were measured in Modulus Luminometer (Knudsen et al., 2008).

Figure 15:
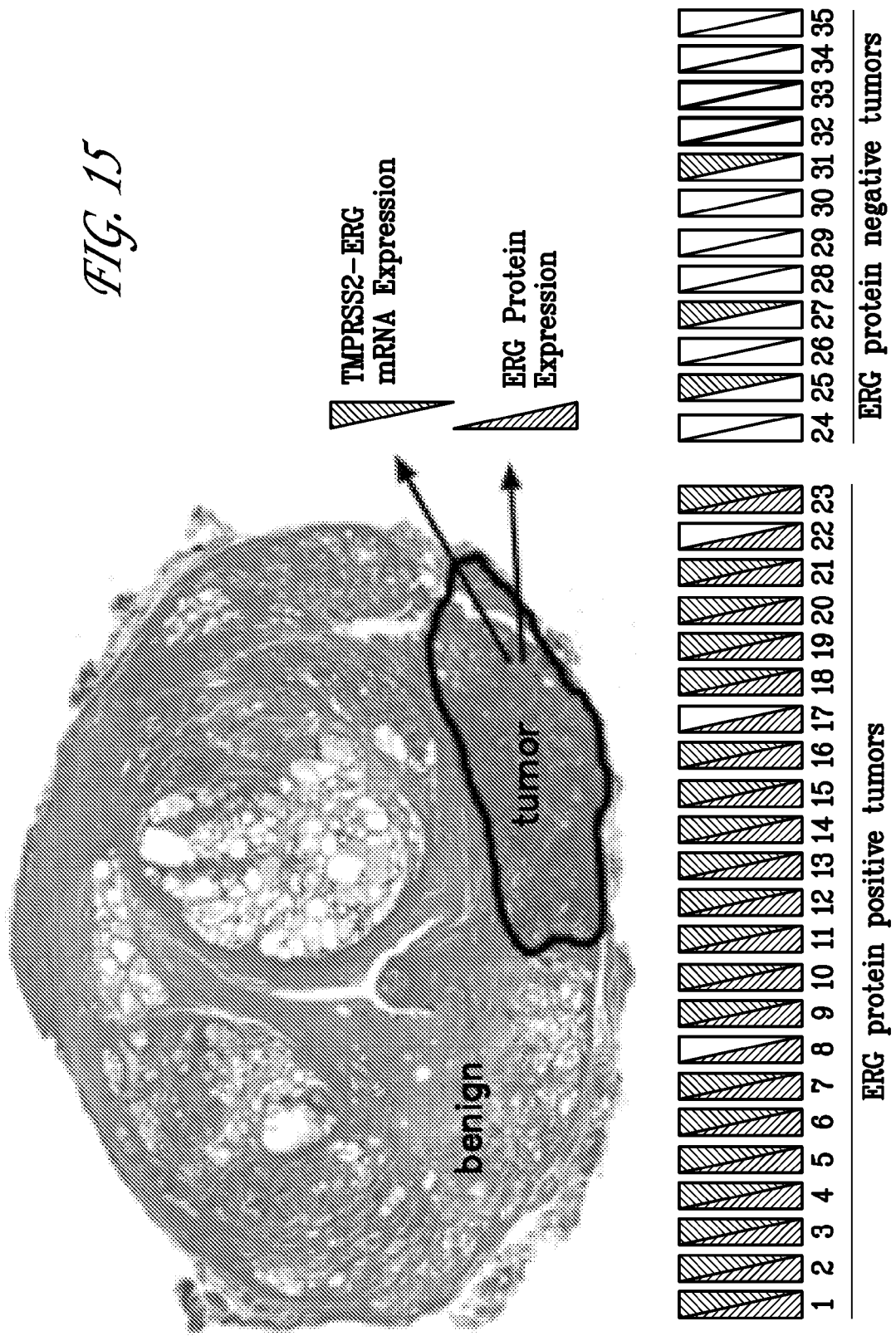
FIG. 15 shows a schematic representation of the expression of ERG oncoprotein (IHC) and TMPRSS2-ERG fusion mRNA in prostate tumors of 35 patients treated with radical prostatectomy by using a branched-chain DNA assay. Consecutive tissue slides from whole mounted FFPE prostate specimens were used for the two assays in a blinded fashion. Backward slash marked triangles represent positive ERG oncoprotein staining, while forward slash marked triangles represent the detection of TMPRSS2-ERG fusion mRNA.

Analysis of 35 evaluable specimens revealed a strong correlation between mRNA levels of TMPRSS2-ERG fusion type A transcript and ERG oncoprotein immunohistochemistry (FIG. 15). A concordance of 82.8% between mRNA and protein data was evident despite the expected differences in the sensitivity as well as read-outs of the two techniques. A comparative evaluation of TMPRSS2-ERG gene fusion analysis by fluorescence in situ hybridization (FISH) and ERG oncoprotein expression by IHC (using the 9FY antibody) also supported these findings and revealed no discrepancies.

Example 8. Expression Map of ERG Oncoprotein in Multi-Focal Prostate Cancer

Prevalent gene fusions involving regulatory sequences of the androgen receptor (AR) regulated prostate associated genes (predominantly TMPRSS2 and to a lesser extent SLC45A3 and NDRG1) and protein coding sequences of nuclear transcription factors in the ETS gene family (primarily ERG), result in frequent overexpression of ERG in prostate tumors. Emerging studies suggest oncogenic functions of ERG and ETV in prostate cancer (CaP) (reviewed in Kumar-Sinha, C. et al., 2008; Klezovitch, O. et al., 2008; Sun, C. et al., 2008; Tomlins, S. A. et al., 2008; Carver, B. S. et al., 2009; King, J. C. et al., 2009; Zong, Y. et al., 2009). Previous studies including our report have analyzed ERG gene fusions at genomic or mRNA levels in the context of multi-focal cancer and these data showed inter-tumoral heterogeneity within the same prostate (Clark, J. et al., 2007; Barry, M. et al., 2007; Mehra R. et al. 2007; Furusato, B. et al., 2008). Despite numerous reports of gene fusions and mRNA expression, ERG oncoprotein in CaP still remains to be defined.

A monoclonal antibody directed against the ERG 42-66 epitope was used to analyze ERG oncoprotein expression in the context of multi-focal CaP. The radical prostatectomy specimens of 132 patients enrolled in a Center for Prostate Disease Research program were obtained by pathologists within 30 minutes after the specimen was surgically removed. The prostates were processed as whole-mounts as discussed above in Example 7 From each patient, one whole mount cross section containing one to four tumors (mostly two foci) was selected and tumors represented different grades and stages. Each tumor was separately diagnosed in the prostatectomy specimens and slices with more than one tumor focus represented separate tumors.

Each tumor was individually measured and graded. On average, one whole mount section (3.5×2.5 cm or 4.0×3.5 cm) is equivalent to approximately 800-1400 tissue microarray cores of 1 mm diameter. In addition to index tumors, most of these cross sections contained benign prostatic tissue of the peripheral and the transition/periurethral zone as well as the urethra, utricle, ejaculatory ducts, and seminal vesicles. A single tumor was present in 51 sections, and multiple individual tumors were present in 81 sections. Tumor grade, pathologic stage, margin status and clinical data are summarized in Table 1.

TABLE 1

Clinico-pathological features for 132 prostate cancer patients

A

| Variables | n | % |
| --- | --- | --- |
| Race | | |
| Caucasian | 105 | 79.6 |
| African American | 27 | 20.4 |
| Pathological T stage | | |
| pT2 | 34 | 25.8 |
| pT3-4 | 84 | 63.6 |
| pT2r1(x) [1] | 14 | 10.6 |
| Prostatectomy Specimen-Gleason Score [2] | | |
| 6 | 33 | 25.6 |
| 7 | 59 | 45.7 |
| 8 to 10 | 37 | 28.7 |
| Margin status | | |
| Negative | 70 | 59.3 |
| Positive | 48 | 40.7 |
| Tumor grade [3] | | |
| Gleason pattern 3 (Well diff.) | 160 | 61.3 |
| Gleason pattern 4/5 (Moderately/Poorly diff) | 101 | 38.7 |

TABLE 1-continued

Clinico-pathological features for 132 prostate cancer patients

Biochemical recurrence [4]

| | n | % |
|---|---|---|
| No | 76 | 65.5 |
| Yes | 40 | 34.5 |

B

| Variables | n | Mean ± SD | Median (range) |
|---|---|---|---|
| Age at surgery (year) | 132 | 61.1 ± 7.4 | 62.3 (40.2-75.2) |
| Pretreatment PSA ng/ml | 132 | 7.7 ± 4.8 | 6.4 (1.1-31.4) |
| Total tumor volume (cc) | 132 | 10.4 ± 9.4 | 7.2 (0.03-52.8) |
| Follow up months after surgery | 130 | 66.5 ± 35.6 | 67.6 (2.7-159.3) |

Table 1. Clinico-Pathological Features of Prostate Cancer Patients.

(A) Demographics and clinico-pathological features (categorical) of prostate cancer patients. [1]Data from patients with pT2r1(x) tumors were not used in this analysis. [2]Corresponds to Gleason score of the index tumor represented in the section except for three patients (Case number 83, 112 and 132). [3]Histological appearance in the observed areas. [4]Two consecutive PSAs≥0.2 ng/ml. (B) Demographics and clinico-pathological features (continuous) of prostate cancer patients.

In both prostatic adenocarcinomas and in PIN, the epithelial cells showed nuclear staining. ERG was positive in 117 of 261 (44.8%) individual tumors (Table 2). Nuclear ERG staining is virtually absent in benign epithelial cells with only 22 of about 200,000 individual benign glands staining ERG positive, demonstrating the remarkable specificity (>99.9%) of this ERG monoclonal antibody in detecting ERG-positive carcinoma (Table 2). The number of benign glands represents an estimate based on counting of the number of benign glands in three average size sections of this cohort (average 1550 benign glands/section) multiplied by 132 sections.

TABLE 2

Frequency of ERG Oncoprotein Expression in Whole Mounted Prostatectomy Specimens

| ERG | Individual Tumors | Benign Glands |
|---|---|---|
| Positive | 117 | 22 |
| Negative | 144 | 200,000 |

Specificity = 99.99%;
Sensitivity = 44.83%;
PPV 84.17%;
NPV = 99.93%

Of 132 specimens, only six specimens showed rare ERG positive non-malignant cells. In three specimens, a single group of benign glands (average 7 glands, raging from 5 to 8 glands) each was positive for ERG in addition to carcinoma. In three additional specimens, ERG was present in small aggregates of native glands (3 to 5 glands) with increased cellularity and nuclear enlargement and mild atypia, changes previously referred to as "low grade PIN." Eight of the nine anterior/transition zone tumors were negative. In all but five cases, over 85% of tumor cells showed moderate to strong nuclear staining with cytoplasmic blush.

Eighty-two of eighty-five (96.5%) evaluable specimens with ERG positive tumor foci contained ERG positive prostatic intraepithelial neoplasia (PIN) lesions, and all of the ERG positive PIN foci were co-located with ERG positive tumors. PIN is a premalignant proliferation arising within the prostate.

Eighty-one sections contained multiple tumors; in 15 of these all tumors were positive; in 31 all tumor foci were negative; and in 35 some tumors were diffusely positive and others completely negative. Thus, in a multi-focal tumor context, 50 of 81 sections (61.7%) had one or more ERG positive tumors. In the 51 sections containing only one tumor, 36 (70.6%) were ERG positive, and two of these contained clones of completely ERG negative tumor cells embedded in the positive areas. A weak non-discriminatory cytoplasmic staining was observed in all epithelial cell types (prostatic and non-prostatic) which was consistent with the cell line data.

The 9FY antibody consistently detected ERG in the nuclei of all endothelial cells (lympho/vascular), which served as intrinsic positive control for the ERG-IHC assay. ERG expression in endothelial cells has also been noted previously in other contexts, however its significance remains to be defined (Baltzinger M. et al., 1999; Birdsey, G. M. et al., 2008); Ellet, F. et al., 2009). Endothelial cells can be easily identified by ERG positive nucleus without or with very little discernible cytoplasm in contrast to carcinoma in which most of the tumor cells have ERG positive nuclei and easily identifiable cytoplasm. In ERG negative poorly differentiated/Gleason pattern 4 or 5 carcinomas, positive nuclei of endothelial cell generally have a linear, narrow distribution.

Tumor cells with amphophilic cytoplasm were more strongly positive than those with pale or foamy cytoplasm. Three of the four mucin producing tumors were positive for ERG. Only two of the five tumors with a ductal component were positive for ERG. One tumor with vacuolated/signet ring-like appearance was positive for ERG. The focus with lymphoepithelioma-like features was negative.

In all seven patients with lymph node metastases at the time of prostatectomy, the ERG expression mirrored the expression status of the index tumor. Four ERG positive primary tumors had ERG positive metastases, and conversely three ERG negative primary tumors had ERG negative metastases. By FISH assay, ERG positive primary tumors and the corresponding metastases showed identical fusion patterns.

Basal cells, urothelial cells of the prostatic urethra and periurethral prostatic ducts were non-reactive. Ejaculatory ducts, seminal vesicles, nerve bundles, fibromuscular stroma, variants of glandular hyperplasia including microacinar hyperplasia (synonyms: adenosis, atypical adenomatous hyperplasia), sclerosing adenosis, and basal cell hyperplasia were all negative for ERG. Different patterns of atrophy including proliferative inflammatory atrophy and evolving or partial atrophy were also negative for ERG.

Association of the ERG oncoprotein status was evaluated with various clinico-pathological features (Table 1A and B). Although, ERG expression did not show correlation with most clinico-pathologic features, when all of the tumor foci in a given whole-mount section were taken into account, higher Gleason sum and less differentiated tumors showed significant correlation with ERG positive immunostaining (Table 3).

TABLE 3

Association of ERG Oncoprotein Status with Tumor Differentiation and Gleason pattern of Individual Tumors (N = 261)

| Tumor grade | ERG status | | P value |
|---|---|---|---|
| | Negative (N = 144) | Positive (N = 117) | |
| Tumor differentiation | | | |
| Gleason pattern 3 (Well differentiated) | 100 (62.5%) | 60 (37.5%) | 0.0027 |
| Gleason pattern 4/5 (Moderate/Poorly differentiated) | 44 (43.6%) | 57 (56.4%) | |
| Tumor Gleason sum | | | 0.0094 |
| 6 | 100 (62.5%) | 60 (37.5%) | |
| 7 | 26 (41.3%) | 37 (58.7%) | |
| 8-10 | 18 (47.4%) | 20 (52.6%) | |

Statistical Analysis.

Sensitivity and specificity of ERG oncoprotein expression were analyzed for distinguishing all tumor foci from benign glands in 132 whole mounted prostates (227 tumor foci and over 200,000 benign glands). Chi-square test or Fisher exact test were used to examine the association between index tumor ERG oncoprotein status with categorical clinico-pathological features, such as race, pathological T stage, prostatectomy Gleason score and margin status. Chi square test was also used to test the association of ERG oncoprotein status with tumor differentiation for individual tumors. P value of 0.05 was adopted as statistically significant. The SAS version 9.2 was used for all data analysis.

Since the gene fusion events in CaP commonly involve regulatory sequences of androgen regulated prostate associated genes, e.g. TMPRSS2, SLC45A3 or NDRG1 along with protein coding sequences of the nuclear transcription factors in the ETS gene family (ERG. ETV1, ETV4-6 and ELK4), the resultant protein products are ETS related oncogenic transcriptions factors with ERG being the most common (Kumar-Sinha, C. et al.; 2008) A monoclonal antibody directed against the ERG 42-66 epitope exhibits a high degree of specificity and sensitivity in recognizing ERG oncoprotein. Positive nuclear staining for the ERG oncoprotein is highly specific (>99.9%) in identifying tumor cells in 65% of patients. Nuclear ERG staining is virtually absent in benign epithelial cells.

Overall 44.8% of all 261 individual tumors were ERG positive in this cohort, whereas 70.6% of 51 specimens with a single tumor were ERG positive and 62% of 81 specimens with more than one tumor were ERG positive. Overall frequencies of ERG expression in CaP specimens noted here are similar to the reported rate of gene fusions involving ERG locus (Kumar-Sinha, C. et al., 2008; Clark, J. et al., 2007). Further, this study points to the potential contribution of sample bias in assessing frequency of ERG alterations in CaP.

In general, tumors are either homogeneously positive or negative for ERG expression. This study highlights the association (96.5%) of ERG positive PINs with ERG positive tumors. While other studies (Kumar-Sinha, C. et al., 2008; Cerveira et al., 2006; Perner et al., 2007) have shown lower frequency of ERG fusion positive PIN (15-20%), this study of whole-mount prostate sections allows more comprehensive evaluation of PIN and tumors in the context of ERG oncoprotein expression.

The rare ERG positive benign glands and the rare atypical native glands, referred to as low grade PIN, may harbor sub-morphological molecular alterations, particularly in view of their topographical relationship to PIN and/or carcinoma. This finding is in agreement with previous studies reporting the presence of TMPRSS2-ERG fusion transcripts in rare instances of benign prostatic glands (Clark, J. et al., 2007; Furusato, B. et al., 2008). The confirmation of TMPRSS2-ERG fusions in these foci is challenging due to their small size. When considering the high concordance rate between ERG oncoprotein expression and TMPRSS2-ERG gene fusion transcript status, one could employ the ERG IHC as an excellent surrogate marker for gene fusions leading to ERG overexpression. Thus, in addition to complementing genomic and mRNA based assays, ERG oncoprotein detection using the antibodies described herein that bind to the 42-66 epitope provides a significant advance in assessing ERG alterations in CaP. For example, translational products resulting from genomic fusion events of ERG protein coding sequence and regulatory sequence of any 5' fusion partners (TMPRSS2. SLC45A3 and NDRG1) (Petrovics, G. et al., 2005; Han, B. et al., 2008; Pflueger, D. et al., 2009) can be detected by ERG-MAb. On the practical side, evaluation of ERG protein by IHC will be more rapid and informative for morphologic assessment of ERG oncogenic activation in a "front-end" pathology setting.

Among the currently used diagnostic markers, alpha-methylacyl-CoA racemase (AMACR) detects approximately 80% of prostatic carcinomas and a variety of other carcinomas (Hameed, O. et al., 2005). However, the specificity of AMACR is lower than that of the ERG, because 25-30% of benign prostatic glands may stain for AMACR. Thus, inclusion of an antibody that binds to the ERG 42-66 epitope in a diagnostic IHC panel can increase the specificity for tumor detection. The strong positive reaction of the 9FY antibody in endothelial cells highlights many more capillaries in the prostate than were previously appreciated using conventional endothelial cell markers (CD 31, CD 34, and Factor VIII related antigens). This feature of ERG expression could potentially complicate the interpretation of the ERG IHC staining. For example, capillaries in intimate contact with glands may suggest basal cell staining, or dilated capillaries with reactive endothelium may mimic small tumor glands or atrophy. However, this potential complication can be overcome through experience recognizing ERG positive vascular patterns.

While prognostic features of ERG alterations in CaP remain to be better understood, both positive and negative associations have been reported (Kumar-Sinha, C. et al., 2008; Clark, J. et al., 2007). In this evaluation of ERG oncoprotein, when all of the tumor foci in a given whole-mount section were taken into account, higher Gleason sum and less differentiated tumors showed correlation with ERG immunostaining (Table 3). However, there was no significant correlation with progression (data not shown). Considering the ERG expression in the multi-focal tumor context, further independent evaluations in larger and better defined cohorts are warranted.

In summary, among the currently known CaP protein biomarkers the detection of the homogeneous, strong and highly specific ERG oncoprotein offers unprecedented opportunities in CaP diagnostic setting. These findings substantiate the role of ERG activation in clonal selection and expansion of ERG positive tumor cells during the transition from pre-invasive to invasive CaP in two thirds of patients. Finally, with a better understanding of ERG functions in prostate tumor biology, ERG-monoclonal antibody based stratification of prostate tumors in future may be used in the context of imaging, targeted therapy or monitoring efficacy of androgen ablation therapy.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

The following references are cited in the application and provide general information on the field of the invention and provide assays and other details discussed in the application. The following references are incorporated herein by reference in their entirety.

Attard, G. et al. (2008). *Oncogene* 27, 253-263.
Baltzinger, M. et al. (1999). *Dev Dyn* 216, 420-433.
Barry, M. et al. (2007). *Urology* 70, 630-633.
Beach, R. et al. (2002). Am J Surg Pathol 26, 1588-1596.
Birdsey, G. M. et al. (2008). *Blood* 111, 3498-3506.
Carver, B. S. et al. (2009). *Nat Genet* 41, 619-624.
Cerveira, N. et al., (2006) *Neoplasia* 8, 826-832.
Clark, J. et al. (2007). *Oncogene* 26, 2667-2673.
Egevad, L. (2008). *Anal Quant Cytol Histol* 30, 190-198.
Ellett, F. et al. (2009). *Mech Dev* 126, 220-229.
FitzGerald, L. M. et al. (2008). BMC Cancer 8, 230.
Furusato, B. et al. (2008). Mod Pathol 21, 67-75.
Furusato, B. et al. (2008). Prostate Cancer Prostatic Dis 11, 194-197.
Gopalan, A. et al. (2009). *Cancer Res* 69, 1400-1406.
Gupta, A. et al. (2004). Am J Surg Pathol 28, 1224-1229.
Hameed, O et al., (2005). *Am J Surg Pathol* 29, 579-587.
Han, B. et al., (2008) *Cancer Res* 68, 7629-7637.
Hermans, K. G., et al. (2009). *Clin Cancer Res* 15, 6398-6403.
Hu, Y. et al. (2008). Clin *Cancer Res* 14, 4719-4725.
Jiang, Z. et al. (2001). Am J Surg Pathol 25, 1397-1404.
King, J. C. et al., (2009). *Nat Genet* 41, 524-526.
Klezovitch, O. et al. (2008). *Proc Natl* Acad Sci USA 105, 2105-2110.
B. S. Knudsen, A. N. et al. (2008). *J Mol Diagn* 10, 169-176.
Koeffler, H. P., and Golde, D. W. (1978). *Science* 200, 1153-1154.
Kubo, J. et al. (2003). *Am J Pathol* 163, 571-581.
Kumar-Sinha, C. et al. (2008). Nat Rev Cancer 8, 497-511.
Larkin, M. A. et al. (2007). Bioinformatics 23, 2947-2948.
Luo, J. et al. (2002). *Cancer Res* 62, 2220-2226.
McLaughlin, F. et al. (1999). J Cell Sci 112 (Pt 24), 4695-4703.
Mehra, R. et al. (2007). *Cancer Res* 67, 7991-7995.
Mehra, R. et al. (2008). *Cancer Res* 68, 3584-3590.
Minowada, J. et al. (1972). J Natl Cancer Inst 49, 891-895.
Mostofi, F. K. et al. (1992). Cancer 70, 235-253.
Mostofi, F. K. et al. (1993). Cancer 71, 906-932.
Narod, S. A. et al. (2008). Br J Cancer 99, 847-851.
Ng, A. P. et al. (2010). Trisomy of Erg is required for myeloproliferation in
mouse model of Down syndrome *Blood*, in press.
Owczarek, C. M. et al. (2004). Gene 324, 65-77.
Perner, S. et al., (2007). *Am J Surg Pathol* 31, 882-888.
Petrovics, G. et al., (2005). Oncogene 24, 3847-3852.
Pflueger, D. et al. (2009). *Neoplasia* 11, 804-811.
Quinn, L. A. et al. (1979). *Cancer Res* 39, 4914-4924.
Rainis, L. et al. (2005). *Cancer Res* 65, 7596-7602.
Rao, V. N. et al. (1987a). Science 237, 635-639.
Rao, V. N. et al. (1987b). Oncogene Res 2, 95-101.
Reddy, E. S. et al. *Proc Natl* Acad Sci USA 84, 6131-6135.
Rubin, M. A. et al. (2002). JAMA 287, 1662-1670.
Saramaki, O. R. et al. (2008). Clin *Cancer Res* 14, 3395-3400.
Shim et al. (2003). J. Neural Trans. Suppl. 67:39-49.
Sun, C. et al. (2008). Oncogene 27, 5348-5353.
Tomlins, S. A. et al. (2005). Science 310, 644-647.
Tomlins, S. A. et al. (2008). Neoplasia 10, 177-188.
Turner, D. P. and Watson, D. K. (2008). Expert Rev Anticancer Ther 8, 33-42.
Wang et al. *Cancer Res.* (2008). 68, 8516-24.
Winnes, M. et al., (2007). *Oncol Rep* 17, 1033-1036.
Yang, X. J. et al. (2002). Am J Surg Pathol 26, 921-925.
Zong, Y., et al. (2009). *Proc Natl Acad Sci USA* 106, 12465-12470.

What is claimed:

1. A composition comprising a polypeptide having no more than 30 amino acid residues, wherein the polypeptide comprises the amino acid sequence consisting of residues 42-66 of SEQ ID NO: 1, and wherein the composition further comprises an adjuvant.

2. The composition of claim 1, wherein the polypeptide has no more than 25 amino acid residues.

3. The composition of claim 1, further comprising a pharmaceutically acceptable excipient.

4. A method of generating a monoclonal antibody that binds to the ERG 42-66 epitope, comprising administering the composition of claim 1 to a non-human mammal, isolating B cells from the non-human mammal, immortalizing the B cells to create a cell line capable of producing a monoclonal antibody, and selecting the monoclonal antibody that binds to the ERG 42-66 epitope.

5. A composition comprising a polypeptide having no more than 30 amino acid residues, wherein the polypeptide comprises the amino acid sequence consisting of residues 42-66 of SEQ ID NO: 1, and wherein the composition further comprises a hapten coupled to the polypeptide.

6. The composition of claim 5, wherein the polypeptide has no more than 25 amino acid residues.

7. The composition of claim 5, further comprising a pharmaceutically acceptable excipient.

8. A method of generating a monoclonal antibody that binds to the ERG 42-66 epitope, comprising administering the composition of claim 5 to a non-human mammal, isolating B cells from the non-human mammal, immortalizing the B cells to create a cell line capable of producing a monoclonal antibody, and selecting the monoclonal antibody that binds to the ERG 42-66 epitope.

9. The composition of claim 1, wherein the polypeptide consists of amino acid residues 42-66 of SEQ ID NO: 1.

10. The composition of claim 5, wherein the polypeptide consists of amino acid residues 42-66 of SEQ ID NO: 1.

11. The composition of claim 1, wherein the polypeptide consists of amino acid residues 42-66 of SEQ ID NO: 1 and a cysteine residue added at the N-terminus or C-terminus.

12. The composition of claim 5, wherein the polypeptide consists of amino acid residues 42-66 of SEQ ID NO: 1 and a cysteine residue added at the N-terminus or C-terminus.

* * * * *

SEQUENCE LISTING

```
<160> NUMBER OF SEQ ID NOS: 9

<210> SEQ ID NO 1
<211> LENGTH: 479
<212> TYPE: PRT
<213> ORGANISM: Homo sapiens

<400> SEQUENCE: 1

Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
            20                  25                  30

Met Thr Ala Ser Ser Ser Asp Tyr Gly Gln Thr Ser Lys Met Ser
        35                  40                  45

Pro Arg Val Pro Gln Gln Asp Trp Leu Ser Gln Pro Pro Ala Arg Val
    50                  55                  60

Thr Ile Lys Met Glu Cys Asn Pro Ser Gln Val Asn Gly Ser Arg Asn
65                  70                  75                  80
```

```
Ser Pro Asp Glu Cys Ser Val Ala Lys Gly Lys Met Val Gly Ser
                85                  90                  95
Pro Asp Thr Val Gly Met Asn Tyr Gly Ser Tyr Met Glu Glu Lys His
            100                 105                 110
Met Pro Pro Asn Met Thr Thr Asn Glu Arg Arg Val Ile Val Pro
        115                 120                 125
Ala Asp Pro Thr Leu Trp Ser Thr Asp His Val Arg Gln Trp Leu Glu
    130                 135                 140
Trp Ala Val Lys Glu Tyr Gly Leu Pro Asp Val Asn Ile Leu Leu Phe
145                 150                 155                 160
Gln Asn Ile Asp Gly Lys Glu Leu Cys Lys Met Thr Lys Asp Asp Phe
                165                 170                 175
Gln Arg Leu Thr Pro Ser Tyr Asn Ala Asp Ile Leu Leu Ser His Leu
            180                 185                 190
His Tyr Leu Arg Glu Thr Pro Leu Pro His Leu Thr Ser Asp Asp Val
        195                 200                 205
Asp Lys Ala Leu Gln Asn Ser Pro Arg Leu Met His Ala Arg Asn Thr
    210                 215                 220
Gly Gly Ala Ala Phe Ile Phe Pro Asn Thr Ser Val Tyr Pro Glu Ala
225                 230                 235                 240
Thr Gln Arg Ile Thr Thr Arg Pro Asp Leu Pro Tyr Glu Pro Pro Arg
                245                 250                 255
Arg Ser Ala Trp Thr Gly His Gly His Pro Thr Pro Gln Ser Lys Ala
            260                 265                 270
Ala Gln Pro Ser Pro Ser Thr Val Pro Lys Thr Glu Asp Gln Arg Pro
        275                 280                 285
Gln Leu Asp Pro Tyr Gln Ile Leu Gly Pro Thr Ser Ser Arg Leu Ala
    290                 295                 300
Asn Pro Gly Ser Gly Gln Ile Gln Leu Trp Gln Phe Leu Leu Glu Leu
305                 310                 315                 320
Leu Ser Asp Ser Ser Asn Ser Ser Cys Ile Thr Trp Glu Gly Thr Asn
                325                 330                 335
Gly Glu Phe Lys Met Thr Asp Pro Asp Glu Val Ala Arg Arg Trp Gly
            340                 345                 350
Glu Arg Lys Ser Lys Pro Asn Met Asn Tyr Asp Lys Leu Ser Arg Ala
        355                 360                 365
Leu Arg Tyr Tyr Tyr Asp Lys Asn Ile Met Thr Lys Val His Gly Lys
    370                 375                 380
Arg Tyr Ala Tyr Lys Phe Asp Phe His Gly Ile Ala Gln Ala Leu Gln
385                 390                 395                 400
Pro His Pro Pro Glu Ser Ser Leu Tyr Lys Tyr Pro Ser Asp Leu Pro
                405                 410                 415
Tyr Met Gly Ser Tyr His Ala His Pro Gln Lys Met Asn Phe Val Ala
            420                 425                 430
Pro His Pro Pro Ala Leu Pro Val Thr Ser Ser Ser Phe Phe Ala Ala
        435                 440                 445
Pro Asn Pro Tyr Trp Asn Ser Pro Thr Gly Gly Ile Tyr Pro Asn Thr
    450                 455                 460
Arg Leu Pro Thr Ser His Met Pro Ser His Leu Gly Thr Tyr Tyr
465                 470                 475

<210> SEQ ID NO 2
<211> LENGTH: 107
<212> TYPE: PRT
```

<213> ORGANISM: Artificial Sequence
<220> FEATURE:
<223> OTHER INFORMATION: Description of Artificial Sequence: Synthetic
    polypeptide

<400> SEQUENCE: 2

Glu Asn Val Leu Thr Gln Ser Pro Ala Ile Met Ser Ala Ser Leu Gly
1               5                   10                  15

Glu Lys Val Thr Leu Ser Cys Arg Ala Ser Ser Ser Val Tyr Tyr Met
            20                  25                  30

Phe Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Val Glu Gly Glu
65                  70                  75                  80

Asp Ala Ala Thr Tyr Tyr Cys Leu Gln Phe Ser Thr Ser Pro Trp Thr
                85                  90                  95

Phe Gly Gly Gly Thr Lys Leu Glu Ile Lys Arg
            100                 105

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 3

Gln Ile Gln Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Ile Asn Trp Val Lys Gln Ala Pro Gly Lys Gly Phe Lys Trp Met
        35                  40                  45

Gly Trp Ile Asp Thr Tyr Thr Gly Glu Pro Thr Tyr Val Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Arg Lys Arg Ala Tyr Asp Tyr Glu Ile Tyr Trp Gly Gln Gly Thr
            100                 105                 110

Pro Leu Thr Val Ser Ser
        115

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 4

Ser Ser Val Tyr Tyr
1               5

<210> SEQ ID NO 5

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Gln Phe Ser Thr Ser Pro Trp Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Thr Phe Thr Asn Tyr Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Asp Thr Tyr Thr Gly Glu Pro
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Arg Lys Arg Ala Tyr Asp Tyr Glu Ile Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Gly Gly Gly Ser Gly Gly Gly Gly Ser
1               5                   10                  15
```